(12) United States Patent
Feinbloom et al.

(10) Patent No.: US 11,740,449 B2
(45) Date of Patent: Aug. 29, 2023

(54) MULTIPLE LIGHT SOURCE CONFIGURATION

(71) Applicant: Designs for Vision, Inc., Bohemia, NY (US)

(72) Inventors: Richard E. Feinbloom, New York, NY (US); Carl A. Giordano, Valley Cottage, NY (US)

(73) Assignee: Designs for Vision, Inc., Bohemia, NY (US)

( * ) Notice: Subject to any disclaimer, the term of this patent is extended or adjusted under 35 U.S.C. 154(b) by 0 days.

(21) Appl. No.: 17/744,711

(22) Filed: May 15, 2022

(65) Prior Publication Data

US 2022/0269065 A1 Aug. 25, 2022

Related U.S. Application Data

(63) Continuation of application No. 17/527,130, filed on Nov. 15, 2021, now Pat. No. 11,359,798, which is a
(Continued)

(51) Int. Cl.
*G02B 25/02* (2006.01)
*F21V 21/084* (2006.01)
(Continued)

(52) U.S. Cl.
CPC ............ *G02B 25/02* (2013.01); *A61B 5/0017* (2013.01); *A61B 5/0077* (2013.01);
(Continued)

(58) Field of Classification Search
CPC ...... G02B 25/02; G02B 5/208; G02B 25/004; G02B 25/008; A61B 90/30; A61B 90/35;
(Continued)

(56) References Cited

U.S. PATENT DOCUMENTS 5,838,247 A 11/1998 Bladowski
7,682,042 B2 * 3/2010 Feinbloom .............. F21V 23/00
362/240

(Continued)

FOREIGN PATENT DOCUMENTS

DE 102007049345 7/2009
EP 3900608 10/2021

(Continued)

OTHER PUBLICATIONS

Extended European Search Report, dated Jun. 3, 2022.

*Primary Examiner* — Bao Q Truong
(74) *Attorney, Agent, or Firm* — Law Office of Carl Giordano, PC

(57) ABSTRACT

A lighting device comprising a plurality of lighting modules arranged concentrically about an optical axis is disclosed wherein the plurality of lighting modules emit light in at least one of a plurality of wavelength ranges (UV, visible (e.g., blue, green, yellow, orange, red, white, etc.), IR) and are arranged at a non-parallel angle to an optical axis of the lighting device, wherein the emitted light is directed towards a lens system that focuses the light onto a viewing point. A second lighting device is disclosed, wherein the lighting device comprises a plurality of lighting modules arranged concentrically about an inner circumference of the lighting device, wherein the plurality of lighting modules emit light in at least one of a plurality of wavelength ranges (UV, visible (e.g., blue, green, yellow, orange, red, white, etc.), IR) onto a lighting director device that redirects the emitted light toward a lens system that focuses the light onto a viewing point.

10 Claims, 17 Drawing Sheets

Related U.S. Application Data continuation of application No. 17/233,467, filed on Apr. 17, 2021, now Pat. No. 11,231,165.

(60) Provisional application No. 63/013,487, filed on Apr. 21, 2020.

(51) Int. Cl.

| | | |
|---|---|---|
| *F21V 23/04* | (2006.01) | |
| *G02B 25/00* | (2006.01) | |
| *G02B 5/20* | (2006.01) | |
| *A61B 90/30* | (2016.01) | |
| *A61B 5/00* | (2006.01) | |
| *A61B 90/35* | (2016.01) | |
| *A61B 90/50* | (2016.01) | |
| *F21V 5/00* | (2018.01) | |
| *F21V 5/04* | (2006.01) | |
| *F21V 7/04* | (2006.01) | |
| *F21V 11/08* | (2006.01) | |
| *F21V 19/02* | (2006.01) | |
| *F21V 23/00* | (2015.01) | |
| *F21V 14/02* | (2006.01) | |
| *G02C 7/08* | (2006.01) | |
| *F21Y 113/10* | (2016.01) | |
| *F21Y 115/10* | (2016.01) | |

(52) U.S. Cl.
CPC ............ *A61B 5/7225* (2013.01); *A61B 90/30* (2016.02); *A61B 90/35* (2016.02); *A61B 90/50* (2016.02); *F21V 5/008* (2013.01); *F21V 5/04* (2013.01); *F21V 7/041* (2013.01); *F21V 11/08* (2013.01); *F21V 14/02* (2013.01); *F21V 19/02* (2013.01); *F21V 21/084* (2013.01); *F21V 23/003* (2013.01); *F21V 23/04* (2013.01); *G02B 5/208* (2013.01); *G02B 25/004* (2013.01); *G02B 25/008* (2013.01); *A61B 5/0071* (2013.01); *A61B 5/0088* (2013.01); *A61B 2090/309* (2016.02); *A61B 2090/502* (2016.02); *A61B 2560/0214* (2013.01); *F21Y 2113/10* (2016.08); *F21Y 2115/10* (2016.08); *G02C 7/086* (2013.01)

(58) Field of Classification Search
CPC ...... A61B 90/50; A61B 5/0017; A61B 5/0077; A61B 5/7225; F21V 5/008; F21V 5/04; F21V 7/041; F21V 11/08; F21V 14/02; F21V 19/02; F21V 21/084; F21V 23/003; F21V 23/04
See application file for complete search history.

(56) References Cited

U.S. PATENT DOCUMENTS

| | | | |
|---|---|---|---|
| 8,851,709 B2* | 10/2014 | Feinbloom | F21V 14/045 |
| | | | 362/802 |
| 9,068,716 B2* | 6/2015 | Kang | F21V 7/0058 |
| 10,247,384 B1 | 4/2019 | Feinbloom | |
| 2007/0097703 A1* | 5/2007 | Goldfain | F21V 13/14 |
| | | | 362/800 |
| 2010/0309646 A1* | 12/2010 | Morikawa | F21K 9/68 |
| | | | 362/235 |
| 2012/0002416 A1 | 1/2012 | Kong | |
| 2014/0334159 A1* | 11/2014 | Ferguson | A61B 90/30 |
| | | | 362/311.09 |

FOREIGN PATENT DOCUMENTS

| | | |
|---|---|---|
| KR | 1020070090542 | 11/2009 |
| WO | 2009/138228 | 11/2009 |

* cited by examiner

MULTIPLE LIGHT SOURCE CONFIGURATION

CLAIM OF PRIORITY

This application claims, pursuant to 35 USC 120, as a Continuation application, priority to and the benefit of the earlier filing date of patent application Ser. No. 17/527,130, filed on Nov. 15, 2022, which claimed, as a Continuation application, priority to, and the benefit of the earlier filing date of patent application Ser. No. 17/233,467, filed on Apr. 17, 2021 (U.S. Pat. No. 11,231,165, which claimed priority to and the benefit of the earlier filing date, pursuant to 35 USC 119, as a non-provisional application, of patent application Ser. No. 63/013,487, filed on Apr. 21, 2020, the contents of all of which are incorporated by reference, herein.

BACKGROUND OF THE INVENTION

Field of the Invention

This application is related to the field of lighting and more particularly a system for providing uniform light distribution from a plurality of light sources

RELATED APPLICATION

This application is related to the U.S. Pat. Nos. 7,682,042; 8,851,709; RE 46463; U.S. Pat. Nos. 9,791,138; 10,240,769; 10,247,384; 10,527,254, and U.S. patent application Ser. Nos. 16/693,212 and 17/233,543, the contents of all of which are incorporated by reference, herein.

BACKGROUND

Lighting devices are typically used in dental, medical and/or surgical fields to allow practitioners (e.g., dentist, doctor, surgeons, etc.) to apply light directly to the area where the practitioner is viewing. Some lighting devices may be free-standing lamps that a practitioner may position about the work area. Other lighting devices may be overhead lighting devices that operate on an arm that the practitioner may position about the work area. User-wearable (e.g., head-mounted) lighting devices may also be used by a practitioner to provide a tight light beam directly coincident with the practitioner's line of sight. Head-mounted lighting devices are advantageous as the projected light is directly at the focus of the practitioner's eyes and the practitioner's shadow is not projected onto the work area as in the case of overhead lights. Operation of such head-mounted devices is known in the art. For example, U.S. Pat. No. 8,851,709; RE46463; U.S. Pat. Nos. 9,791,138; 10,240,769; and 10,527,254, which are assigned to the Assignee of the instant application, disclose user-wearable (e.g., head mounted) devices and their operation. Similarly, U.S. Pat. No. 7,682,042, which is assigned to the Assignee of the instant application, discloses an overhead or lamp configuration. The contents of all of which are incorporated by reference, herein.

Typically, with a head mounted lighting device, a practitioner (e.g., a dentist, a doctor, a surgeon) adjusts the lighting element such that the light is projected onto a surface to which the practitioner's eyes are focused. The practitioner may then control the light output in a manner as disclosed in the aforementioned US patents.

In addition to projecting a light (such as a white light) for assisting the practitioner in viewing the targeted area, the light source may be composed of different lighting sources that may be used for different purposes. For example, the light sources may generate an ultra-violet light (non-visible wavelength range), a visible light (e.g., white, red, green, blue, etc.) or an Infra-red (IR) (non-visible wavelength), wherein the specific wavelength band may achieve a desired purpose. For example, some light wavelengths are known to decrease the time of gel-like materials to harden. In addition, the lighting devices may comprise one or more of the different light sources may be generating a corresponding light concurrently; the control of which may require wired or wireless control circuitry.

However, user-wearable devices are required to be compact and lightweight, which limits the number light emitting elements that may be used in emitting a light. The limited number of lighting emitting elements limits the overall intensity of the light outputted by the head-mounted lighting device.

Hence, there is a need in the industry for a system that allows for a greater emission distribution of light from lighting devices; particularly of the user-wearable kind.

SUMMARY OF THE INVENTION

In accordance with the principles of the invention, there is disclosed a lighting device for the generation of light from multiple lighting sources that provides a greater emission of the light from lighting devices.

In accordance with the principles of the invention, there is disclosed a lighting device comprising a plurality of lighting sources, wherein each of the lighting sources is configurable to provide light to a desired point or region.

In accordance with the principles of the invention, there is disclosed a lighting device comprising a plurality of lighting sources, wherein the lighting sources may be individually controlled while the light outputted by each of the lighting sources may be directed to a desired point or region In accordance with the principles of the invention, there is disclosed a lighting device comprising a plurality of lighting sources, wherein the lighting sources may be controlled electronically and physically to direct a light to a desired point or region In accordance with the principles of the invention, there is disclosed a lighting system that allows for the mixing of light from a plurality of lighting sources, wherein the light is focused onto at a desired point or region.

In accordance with the principles of the invention, there is disclosed a lighting system comprising a plurality of lighting sources arranged concentrically about a central or optical axis of a lens system wherein the lighting sources are oriented with respect to the central axis such that the light emitted by the light sources targets the lens system at a point or region where the lens system projects the light to a desired focal point.

In accordance with the principles of the invention, there is disclosed a lighting system comprising a plurality of lighting sources arranged substantially perpendicular to a central or optical axis of a lens system, wherein the light emitted by the lighting sources targets a light director that re-directs the emitted light to the lens system at a point or region where the lens system projects the light to a desired focal point.

In accordance with the principles of the invention, there is disclosed a lighting device comprising a plurality of lighting sources arranged substantially skewed from an axis perpendicular to a central axis of a lens system, wherein the light emitted by the lighting sources targets a light director that re-directs the emitted light to the lens system at a point or region where the lens system projects the light to a desired focal point.

In accordance with the principles of the invention, there is disclosed a lighting system comprising a plurality of lighting sources that are arranged to emit light individually, concurrently or sequentially in one of more light wavelength bands toward a light director, which redirects the light to a lens system that projects the light to a desired focal point.

BRIEF DESCRIPTION OF DRAWINGS

For a better understanding of exemplary embodiments and to show how the same may be carried into effect, reference is made to the accompanying drawings. It is stressed that the particulars shown are by way of example only and for purposes of illustrative discussion of the preferred embodiments of the present disclosure and are presented in the cause of providing what is believed to be the most useful and readily understood description of the principles and conceptual aspects of the invention. In this regard, no attempt is made to show structural details of the invention, or in a scale, in more detail than is necessary for a fundamental understanding of the invention, the description taken with the drawings making apparent to those skilled in the art how the several forms of the invention may be embodied in practice. In the accompanying drawings.

It is to be understood that the figures and descriptions of the present invention described herein have been simplified to illustrate the elements that are relevant for a clear understanding of the present invention, while eliminating for purposes of clarity, many other elements. However, because these omitted elements are well-known in the art, and because they do not facilitate a better understanding of the present invention, a discussion of such elements is not provided herein. The disclosure, herein, is directed also to variations and modifications known to those skilled in the art.

DETAILED DESCRIPTION

Figure 1A:
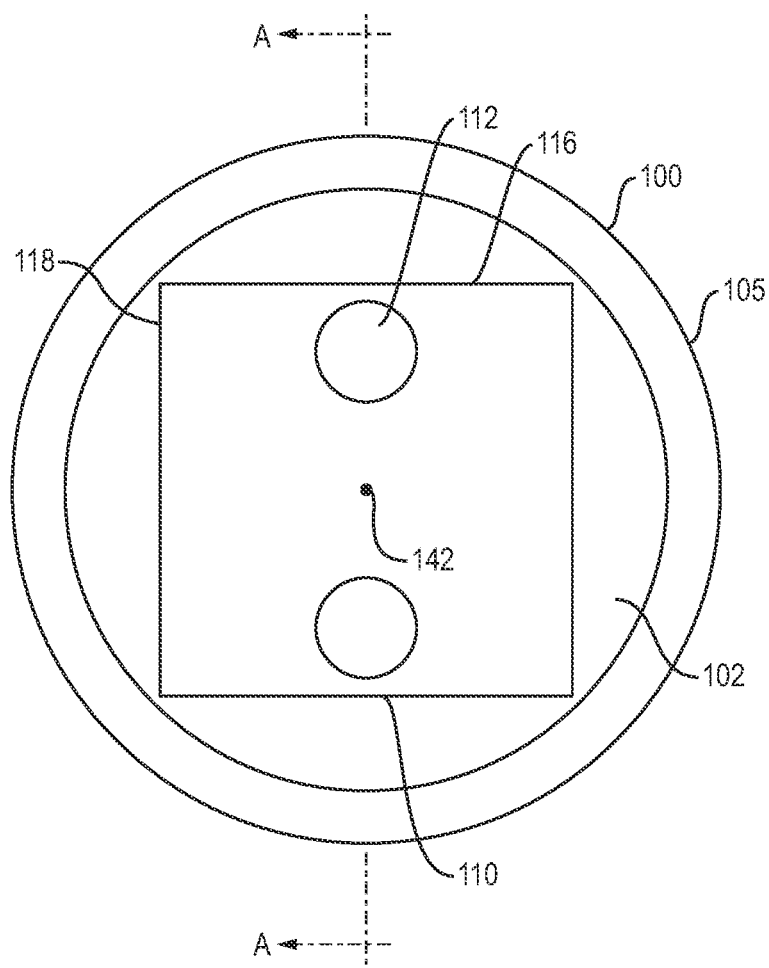
FIG. 1A illustrates a front view of a first exemplary embodiment of a lighting device comprising multiple light sources in accordance with the principles of the invention.

FIG. 1A illustrates a front view of a first exemplary embodiment of a lighting device comprising multiple light sources in accordance with the principles of the invention.

In this illustrated front view, lighting device 100 comprises a housing 105 and a lens 102 through which lighting assembly 118 is visible. Lens 102 closes a distal end of lighting device 100.

Further illustrated are lighting sources 110 and 112 incorporated onto lighting assembly 118, wherein lighting sources 110, 112 are positioned concentrically around or about a central or optical axis 142, which is formed by lens 102.

Lighting sources 110 and 112 are oriented with respect to the central or optical axis 142 to direct the light outputted by the plurality of lighting modules to a point (not shown).

Lighting assembly 118 further includes control unit 116 that controls the operation of the lighting sources 110, 112 to emit light. Control unit 116 may comprise one or more of resistors, transistors, diodes, capacitors that form dedicated hardware configuration and/or specialized hardware (e.g., ASIC, microcontroller, microprocessor) that enable control unit 116 to control the application of electrical energy to one or more of lighting sources 110, 112, etc.

Figure 1B:
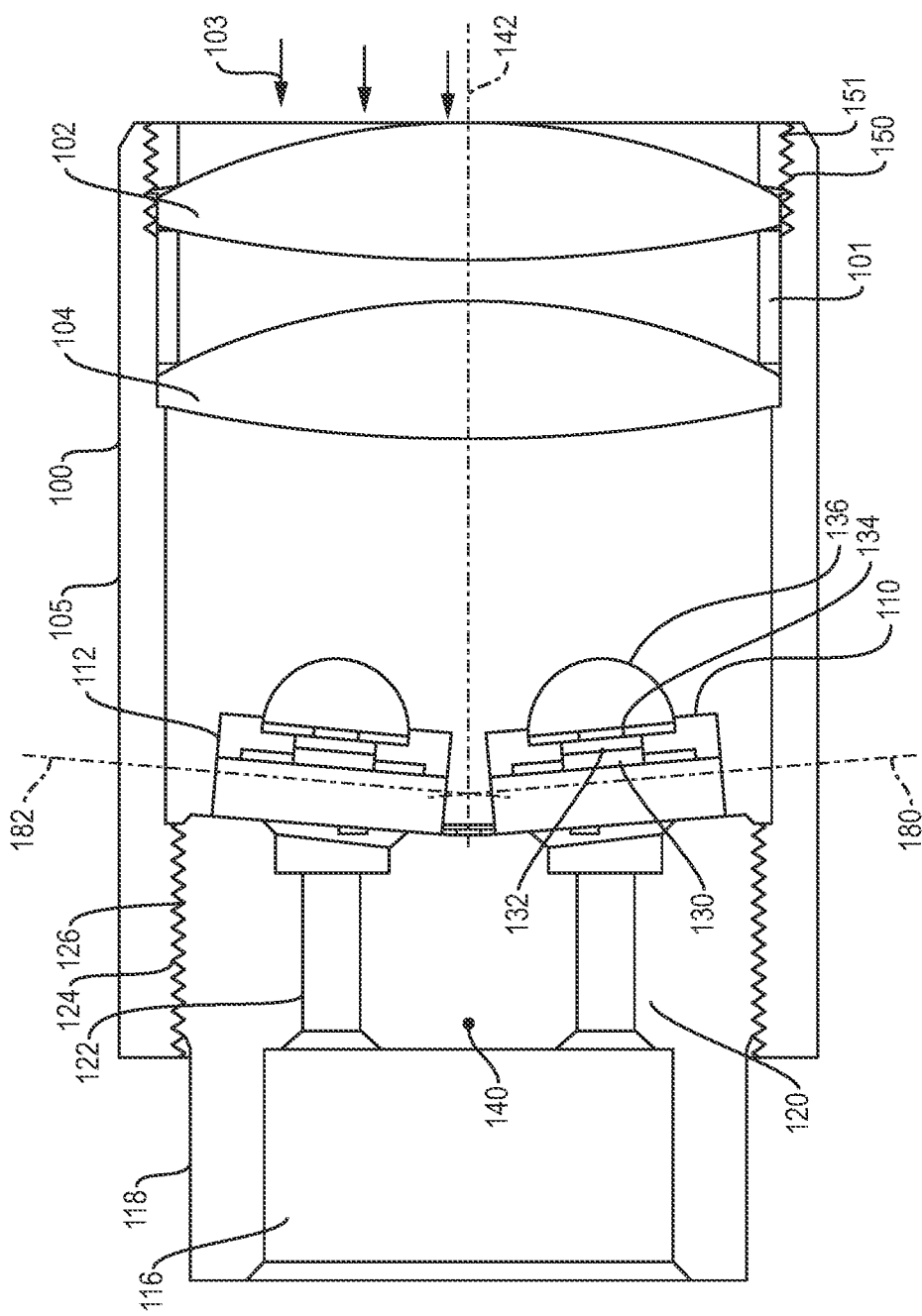
FIG. 1B illustrates a side view, through section A-A, of the first exemplary embodiment of the lighting device shown in FIG. 1A

FIG. 1B illustrates a side view, through section A-A, of the first exemplary embodiment of the lighting device shown in FIG. 1A In this illustrated embodiment, lighting device 100 comprises lighting housing 105 into which lens assembly 101, comprising at least one objective lens 102, 104, is positioned at a first end of lighting housing 105. The at least one objective lens 102, 104 are substantially concentric and define a central or optical axis 142 of lighting device 100. The characteristics of lens 102, 104 form a focal point 140 onto which light 103 passing through lens assembly 101 converges.

Positioned at a second end of lighting housing 105 is lighting (or optical) assembly 118, which comprises control unit 116 and lighting sources 110 and 112. Connection between control unit 116 and lighting sources 110, 112 is provided by arms or extensions 120, 122. Arms 120, 122 provide a means for providing electrical energy to lighting sources 110, 112 and further providing for adjustment of lighting sources 110, 112 to change an angle of orientation of lighting source 110, 112 with respect of central or optical axis 142.

As is further shown, lighting assembly 118 and lens housing 101 may be mountable within light device 100 by a screw-thread connection (i.e., 124/126 150/151, respectively). Although a screw-thread connection is shown, it would be understood that other connections methods may be employed without altering the scope of the invention. For example, a snap-fit or a bayonet connection may be utilized for lighting assembly 118 and/or lens assembly 101.

In accordance with one aspect of the invention, lighting sources 110, 112 comprise holder 130, electronic section (i.e., printed circuit board) 132, light source 134 and lens 136.

Holder 130 provides a means for retaining lighting sources 110 (112) within lighting assembly 118. Electronic section 132 may comprise a printed circuit board, including known components, such as resistors, transistors, capacitors, special hardware circuitry (e.g., ASIC), and/or microcontroller/microprocessor, that control a flow of electrical energy (voltage/current) to light element 134. Light element 134 may comprise light emitting diodes (LEDs) that may possess lasing capability (i.e., semiconductor laser) or non-lasing capability (e.g., super-luminance diodes, etc.). Lens 136 provides for a concentration of the light emitted by light source 134.

A more detailed understanding of a preferred construction of lighting sources 110, 112 may be found in the referred to related US Patents wherein lighting sources 110 comprises at least one of: a lighting element (e.g., a light emitting diode), an aperture holder, an aperture and a dome lens, wherein the aperture holder and aperture are configured to adapt or configure the light outputted by the lighting element and the dome lens is configured to concentrate the light outputted through the aperture.

For example, in the case of the emission of a white light, lighting element 134 may comprise a phosphor layer and a blue die positioned on the phosphor layer wherein the light emitted by light element 134 is primarily a white light. Aperture holder (not shown) may include a passthrough which is sized to allow the blue die element of light element 134 to passthrough, while blocking light emitted by the phosphor layer. An aperture, positioned on or within the aperture holder, may include a passthrough that may be sized to further reduce (adapt or configure) the amount of stray light of the phosphor layer to passthrough the aperture. In one aspect of the invention, the aperture passthrough may be sized to allow the blue die element of the lighting element 134 to passthrough. In another aspect of the invention, the aperture passthrough may be sized to allow only a center region of the blue die element of lighting element 134 to be viewable through the aperture passthrough and prevent the blue die element from being positioned within the aperture passthrough. In one aspect of the invention, the aperture holder passthrough may the substantially square or circular to allow the blue die element to passthrough, while the aperture passthrough may be circular or square and smaller than the blue die element. In addition, in accordance with the principles of the teachings of the related US patents, the lighting element 134 may be within a focal length of the dome lens 136.

Although a specific configuration of lighting sources 110, 112 is disclosed, it would be recognized that lighting source 110, 112 may include only electronic section 132 and light element 134, wherein at least one of the aperture holder, the aperture and dome lens 136 may not be utilized.

Returning to FIG. 1B, arm 120 provides electrical and mechanical connection from control unit 116 to lighting source 110. For example, control unit 116 may provide electrical energy to lighting source 110 such that a light may be emitted by lighting source 110. In one aspect of the invention, a magnitude (i.e., a drive current) of the electrical energy provided to lighting source 110 may be adjusted such that the light output may transition from a low output light to a high output light or from a light ON condition to a light OFF condition.

Extension arm 120 may be adjustable in a manner that changes an orientation of lighting source 110 with respect of optical axis 142.

In this illustrated embodiment lighting source 110 is oriented with respect to an axis 182 wherein axis 182 is offset from an axis (not shown) that is substantially perpendicular to optical axis 142.

In one aspect of the invention, arm 120 may comprise a screw thread (not shown), which when turned in a first (e.g., clockwise) direction may decrease the angle of axis 180 with respect to optical axis 142. Whereas, when turned in a second (e.g., counterclockwise direction), the angle of axis 180 with respect to optical axis 142 may increase.

Alternatively, offset axis 180 may be preset in a manner to satisfy the angle characteristics presented herein, wherein a light emitted by lighting source 110 converges to a point a known distance from lens 102.

Further illustrated is second lighting source 112 positioned opposite optical axis 142. Second lighting source 112 is similar in construction and electrical and physical operation to first lighting source 110 and a detailed discussion of the construction and operation of second lighting source 112 is not believed necessary, as those skilled in the art would understand both the construction and operation of second lighting source 112 from the discussion associated with lighting source 110.

Control unit 116 may further provide electrical energy to one or more of lighting sources 110, 112 in a manner such that the light emitted by lighting sources 110, 112 may be emitted concurrently, individually or sequentially.

Although controller 116 is shown as an individual element, it would be understood that the control function of controller 116 may be incorporated into the electronic components associated with PCB 132.

Hence, the illustrated element 116 may merely comprise a base onto which arms 120, 122 are positioned, and the control function may be included in PCB 132.

Accordingly, the lighting sources 110 and 112 may be referred to as lighting module 110/116 and 112/116 to illustrate the distributive nature of the electronic components associated with controller 116 and PCB 132.

Figure 2:
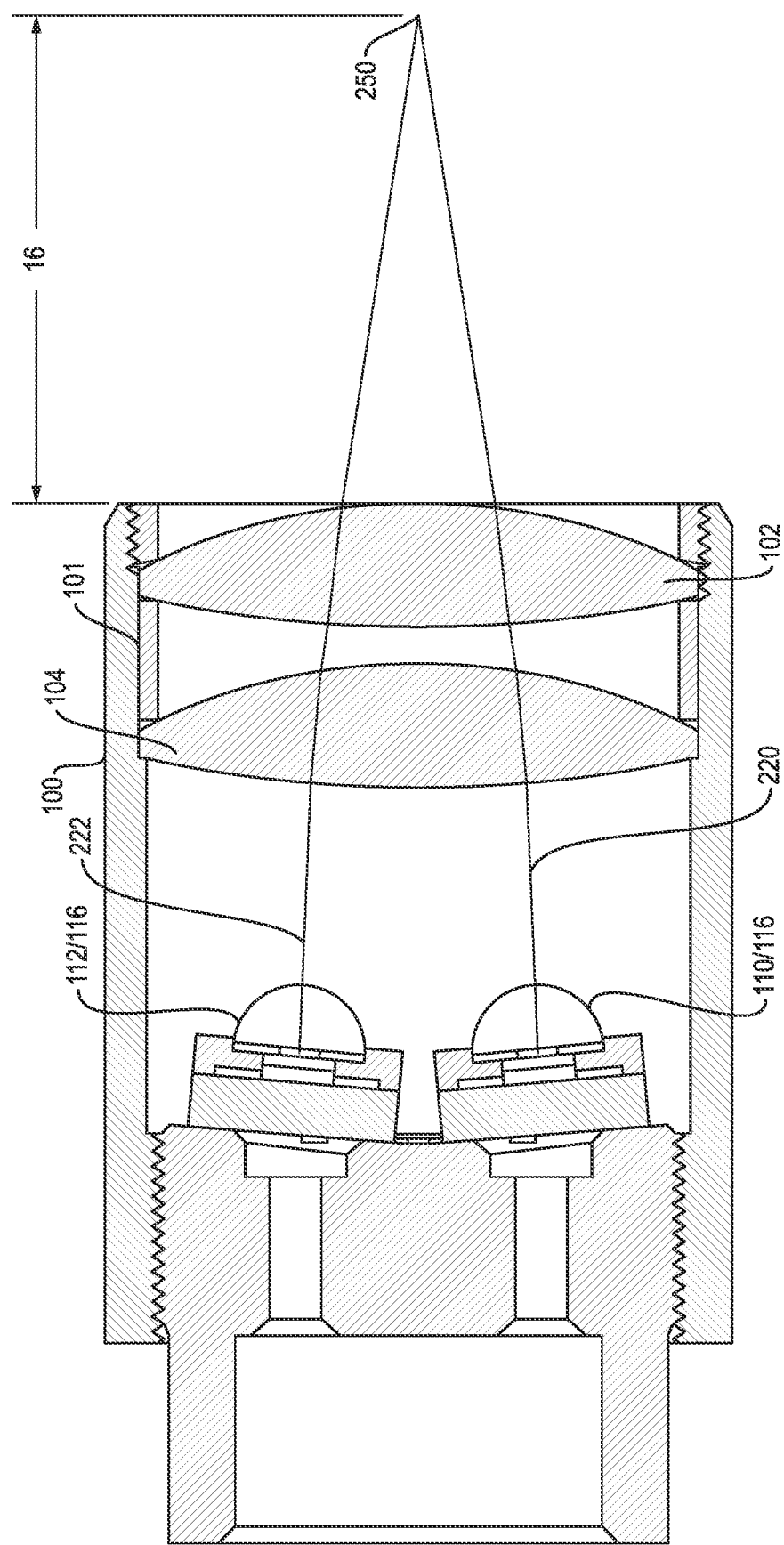
FIG. 2 illustrates a second side view, through section A-A, of the first exemplary embodiment of the lighting device shown in FIG. 1A.

FIG. 2 illustrates a second side view, through section A-A, of the first exemplary embodiment of the lighting device shown in FIG. 1A.

In this illustrated aspect of the invention of lighting device 100, first lighting module 110/116 generates light directed along light path 220 toward lens assembly 101. Similarly, second lighting module 112/116 generates light directed toward lens assembly 101 along light path 222.

The light generated by first lighting module 110/116 and second lighting module 112/116 passes through lens 104 and 102 and converges onto a known point 250. In this case, known point 250 is illustrated to be approximately 16 inches from a lighting device 100.

Although sixteen inches is illustrated as the point of convergence 250 of the light emitted by lighting device 100, it would be understood that the use of the measurement of 16 inches is only to illustrate the convergence of the light and other distances or measurements from lighting device 100 may be achieved by changing the relationship between lighting modules 110/116, 112/116 and lens housing 101. Hence, other distances (or focal points) are considered within the scope of the invention claimed.

Figure 3:
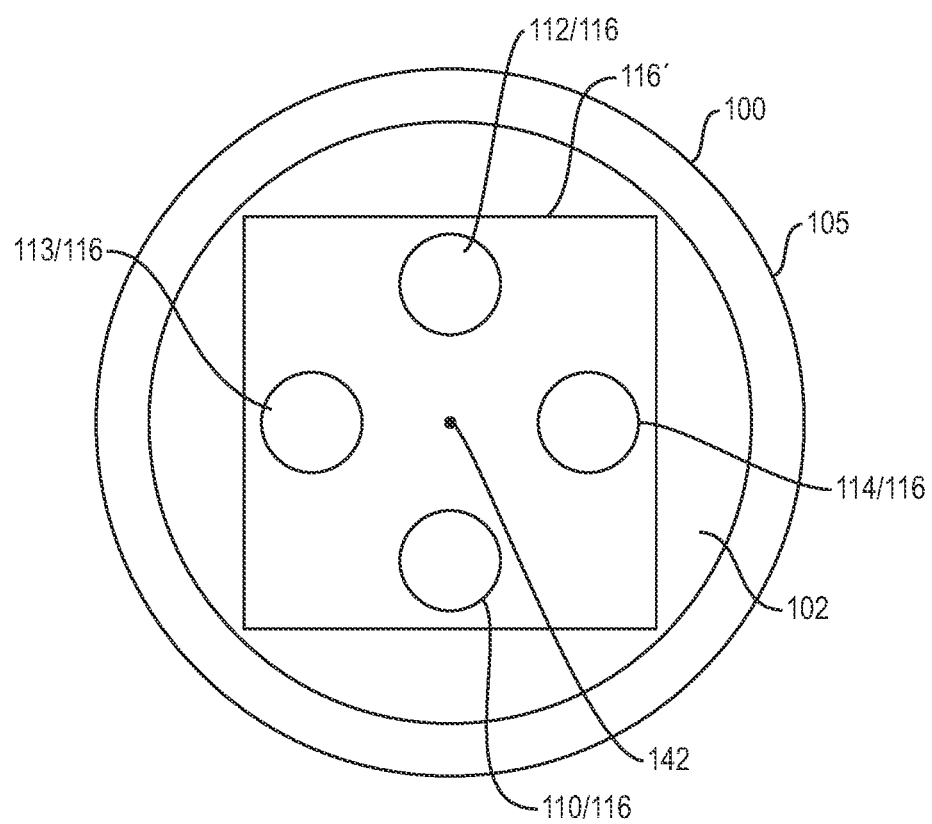
FIG. 3 illustrates a front view of a second aspect of the first exemplary embodiment shown in FIGS. 1A, 1B and 1C.

FIG. 3 illustrates a front view of a second aspect of the first exemplary embodiment shown in FIGS. 1A, 1B and 1C.

In this illustrated front view, a plurality of lighting modules (e.g., first lighting module 110/116, second lighting module 112/116, third lighting module 113/116 and fourth lighting module 114/116) are positioned concentrically around optical axis 142, wherein each of the plurality of lighting modules is attached to corresponding extensions (not shown), which are attached to base 116'. Electrically energy (voltage, current) may be applied to the lighting modules 110/116 . . . 114/116, through extensions (not shown) as previously discussed, wherein the electronic elements of controller 116/PCB 132 control the application of the voltage to corresponding lighting modules.

The plurality of lighting modules 110/116 . . . 114/116 are oriented, as discussed, to direct the light outputted by the plurality of lighting modules to a focus point 250 (not shown).

Although four (4) lighting modules are illustrated, it would be recognized that the number of lighting modules may be increased (i.e., greater than the illustrated 4) or decreased (i.e., 2 or 3) without altering the scope of the invention.

Figure 4A:
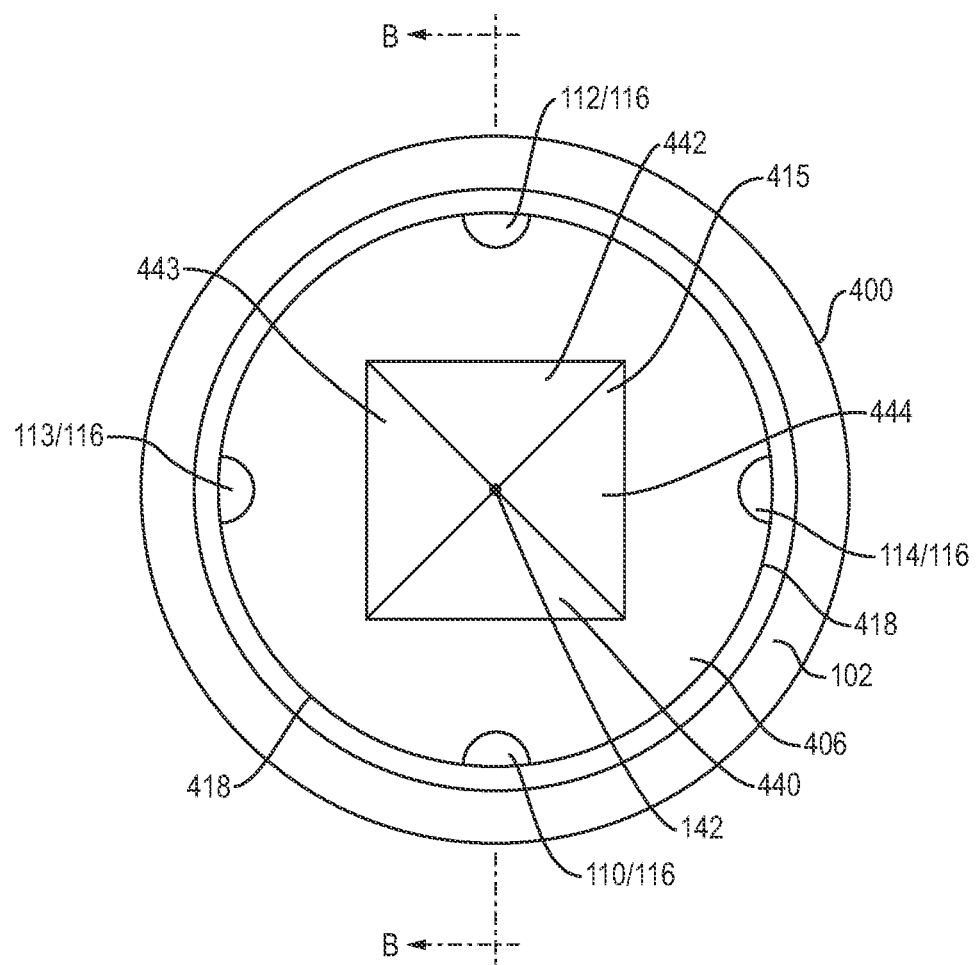
FIG. 4A illustrates a front view of a first aspect of a second exemplary embodiment of a lighting device 400 in accordance with the principles of the invention.

FIG. 4A illustrates a front view of a first aspect of a second exemplary embodiment of a lighting device 400 in accordance with the principles of the invention.

In this illustrated front view of lighting device 400, a plurality of lighting sources and associated distributed controllers (referred to as first lighting module 110/116, second lighting module 112/116, third lighting module 113/116 and fourth lighting module 114/116) are shown positioned along an inner circumference surface of lighting assembly 418. Further illustrated is light director 415 extending from base 406 of lighting assembly 418, wherein light director 415 is in a shape of a 4-sided pyramid. In addition, each of the sides or lateral faces of the illustrated 4-sided pyramid 415 may include a reflective surface (e.g., aluminum, mirror, etc.) 440, 442, 444, 446, that redirects light emitted by one or more of the lighting modules toward lens assembly 101.

In accordance with the principles of the invention, light emitted by lighting modules 110/116, 112/116, 113/116, 114/116 is directed to a corresponding one of the lateral faces (which include reflective surfaces) such that the emitted light, which is in the plane of the paper, is redirected such that the emitted light is directed perpendicular to the plane of the paper. In accordance with the principles of the invention the light emitted by lighting modules 110/116 . . . 114/116 may be emitted individually, concurrently or sequentially.

Figure 4B:
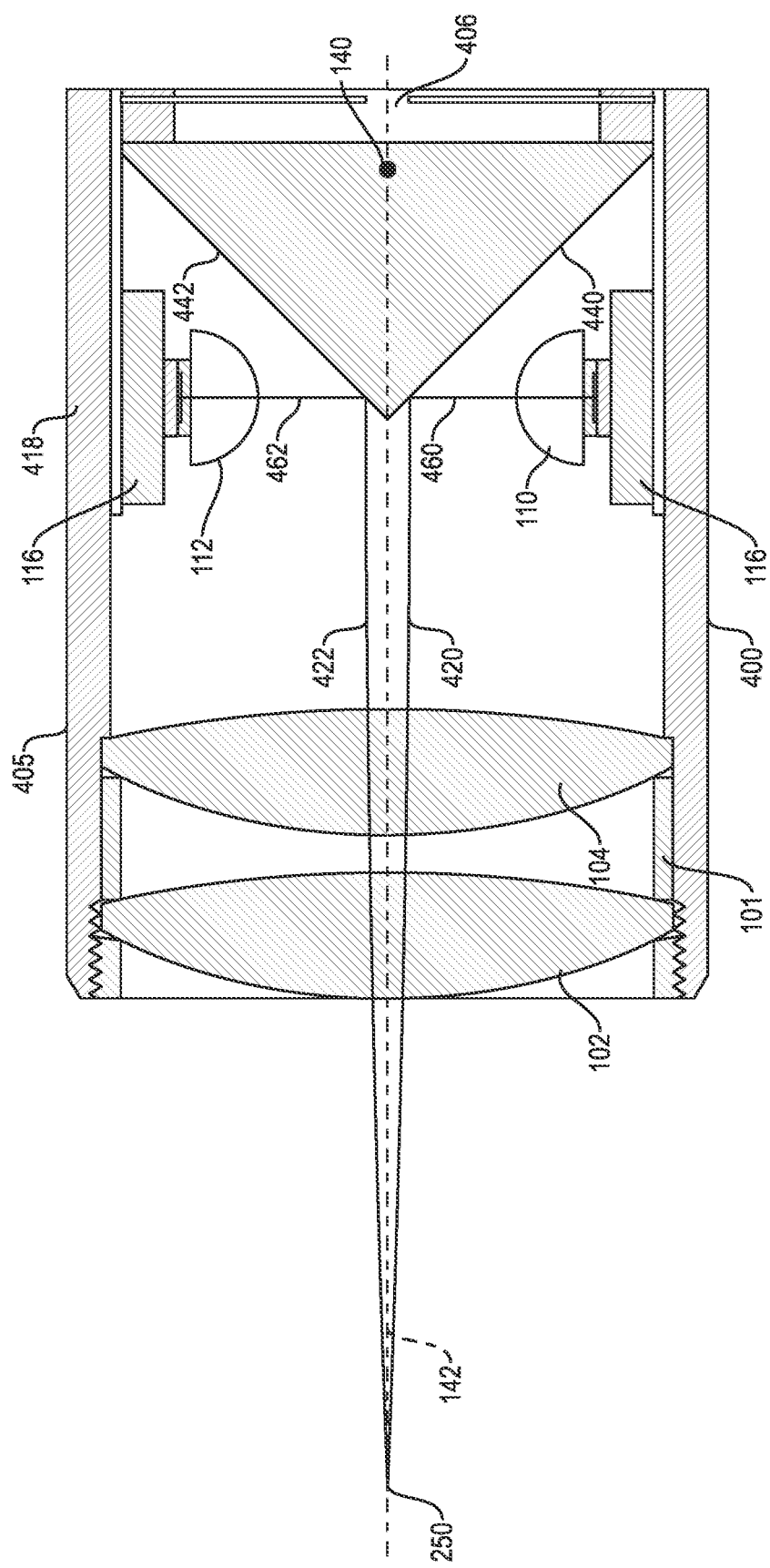
FIG. 4B illustrates a side view, through section B-B, of the first aspect of the second exemplary embodiment of a lighting device shown in FIG. 4A.

FIG. 4B illustrates a side view, through section B-B, of the first aspect of the second exemplary embodiment of a lighting device shown in FIG. 4A.

In this second exemplary embodiment, lighting device 400 comprises a lighting housing 405 comprising lens assembly 101 positioned on a first end of lighting housing 405 and lighting assembly 418 positioned on a second, opposing end of light housing 405. Lens assembly 101 comprises at least one objective lens 102, 104 forming an optical axis 142 on which focal point 250 is formed, as previously discussed.

Further illustrated is lighting assembly 418 comprising a first lighting module 110/116 (as first lighting source 110 and associated controller 116) and second lighting module (second lighting source 112 and associated controllers 116) positioned around or about an inner circumference to lighting assembly 418. The illustrated first lighting source 110 and second lighting source 112 are similar in construction to lighting source 110, 112 shown in, and described, with regard to FIGS. 1A, 1B and 2. Although only two lighting modules are shown, it would be recognized that a greater number of lighting modules may be distributed about the inner surface of lighting assembly 418.

Furthermore, although lighting assembly 418 is shown without a screw thread attachment to housing 405, it would be understood that lighting assembly 418 may be removably attached to lighting housing 405 through at least one of: a screw thread, a snap-fit, a bayonet, etc., type connection in a manner similar to that discussed with regard to lighting assembly 118 shown in FIG. 1B, for example. Alternatively, lighting assembly 418 may be integrated into lighting housing 405.

In this first aspect of the second exemplary embodiment of a multi-light source lighting device, first lighting module 110/116 and second lighting module 112/116, positioned along an internal circumference of lighting assembly 418, emit or generate a light that is substantially perpendicular to optical axis 142 along light path 460, 462, respectively.

Light director 415 operates to receive the emitted light and redirect the light emitted by first lighting module 110/116 and second lighting module 112/116 toward lens assembly 101, along light paths 420, 422, respectively.

In this illustrated embodiment, light director 415 comprises a pyramid shaped element positioned on base 406, wherein the sides or lateral faces of light director 415 extend from base 406 at an angle oriented at substantially a forty-five (45) degree angle with respect to optical axis 142; forming a ninety (90) degree angle at an apex of light director 415, to allow light generated or emitted by first lighting module 110/116 and second lighting module 112/116 to be redirected toward lens assembly.

Light director 415 further comprises reflective surfaces 440, 442, on at least a portion of corresponding one of its lateral surfaces, wherein reflective surfaces 440, 442 operate to redirect a substantial portion of the light generated or emitted by first lighting module 110/116 and second lighting module 112/116 toward lens assembly 101.

In accordance with the principles of the invention, light directed along light paths 420 and 422 is outputted by lens assembly 101 such that the light converges onto known point 250, as previously discussed.

Although, lighting modules 110/116 and 112/116 are shown in a distributed controller configuration, it would be recognized that the controller 116 may be remote from lighting sources 110, 112 as shown in FIG. 1B, for example, without altering the scope of the invention claimed.

Figure 4C:
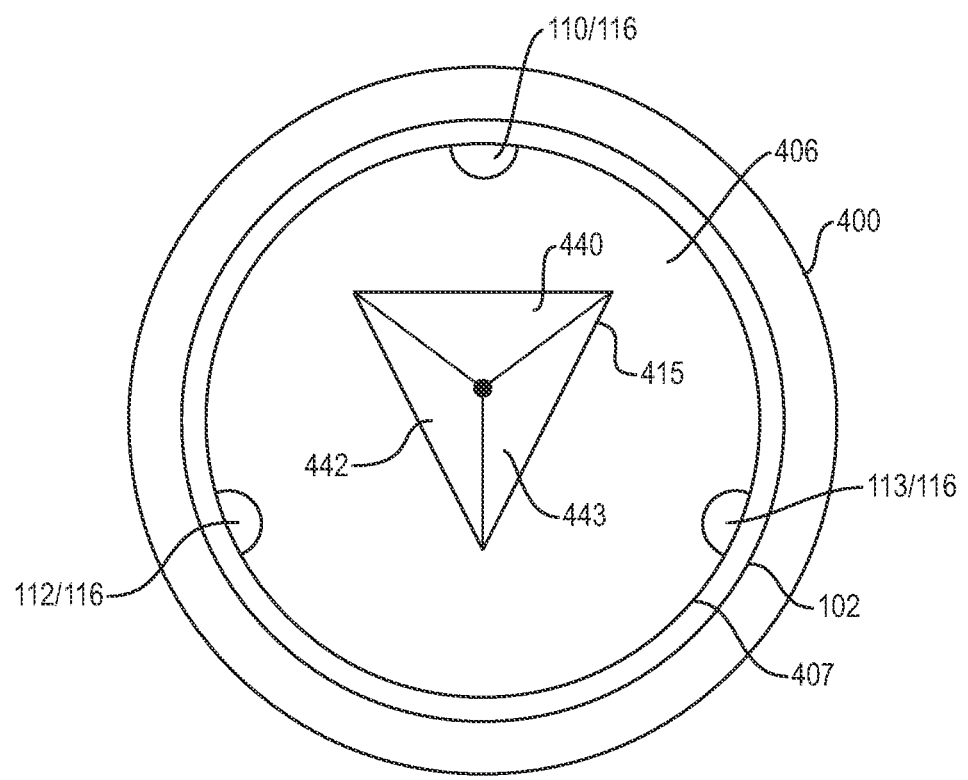
FIG. 4C illustrates a front view of a second aspect of the second exemplary embodiment of a lighting device shown in FIG. 4A.

FIG. 4C illustrates a front view of a second aspect of the second exemplary embodiment of a lighting device shown in FIG. 4A.

In this illustrated front view, a plurality of lighting modules (e.g., first lighting module 110/116, second lighting module 112/116, and third lighting module 113/116) are shown positioned along an inner circumference surface of lighting assembly 418. Further illustrated is light director 415 extending from a base 406 of lighting assembly 418, wherein light director 415 is in a shape of a tetrahedron (i.e., a 3-sided pyramid). In addition, each of the lateral surfaces (or portions thereof) of light director 415 may include a reflective surface 441, 442, 443, respectively, to reflect a substantial portion of the light emitted by corresponding ones of the lighting modules.

As previously discussed, the light emitted by the lighting modules 110/116, 112/116, 113/116, may be emitted concurrently, individually or sequentially.

Although light director 415 shown in FIG. 4A is shown as a 4-sided pyramid and shown in FIG. 4C as a 3-sided pyramid, it would be recognized that a number of sides or lateral faces of light director 415 may be increased without altering the scope of the invention. For example, the number of lateral faces of the light director 415 may be determined based on a number of lighting modules positioned along the inner circumference surface of lighting assembly 418. Alternatively, light director 415 may include an infinite number of sides (i.e., a cone or conical shape), which is independent of the number of lighting modules.

Figure 5A:
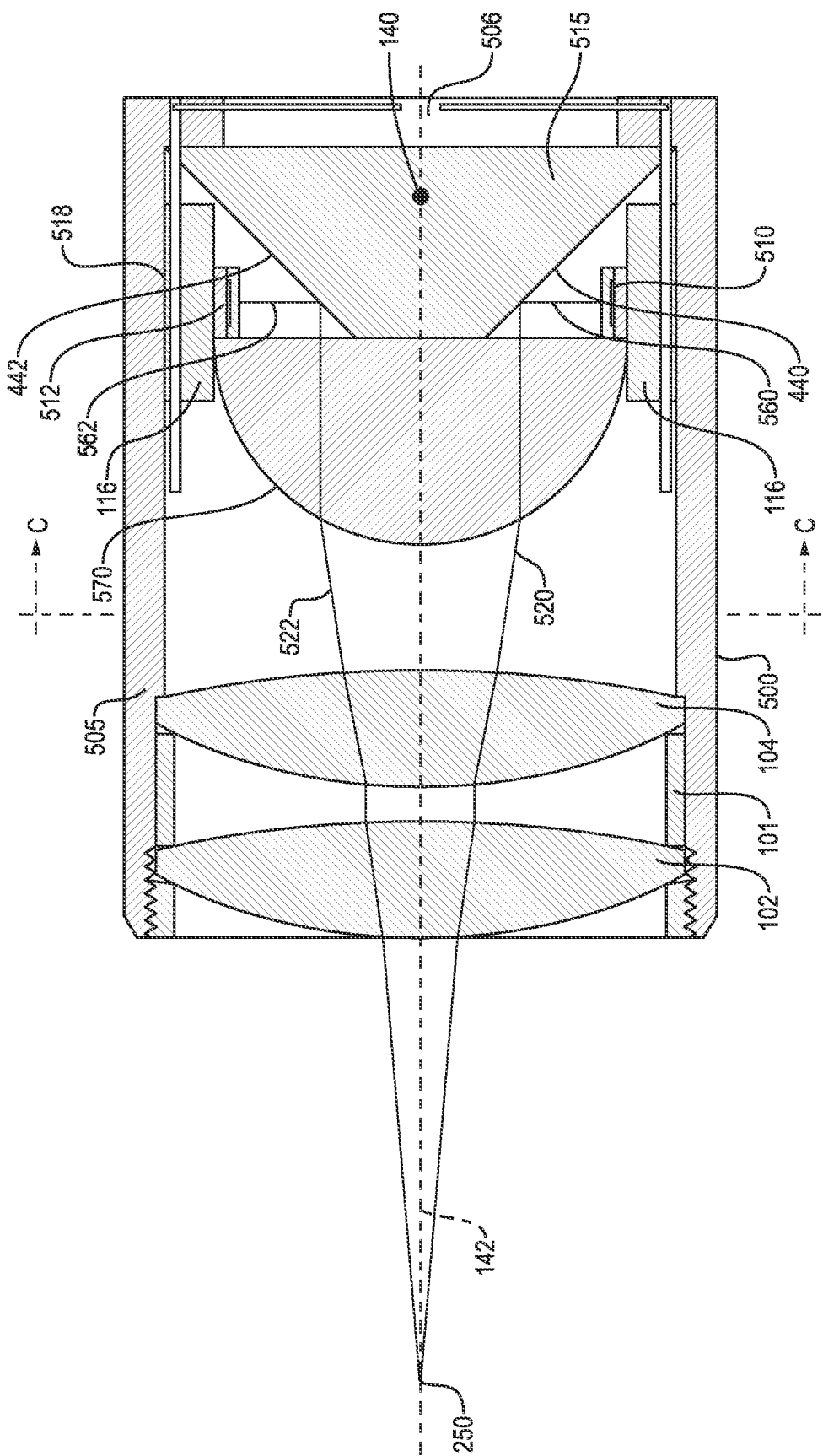
FIG. 5A illustrates a side view of a first aspect of a third exemplary embodiment of a lighting device comprising multiple light sources in accordance with the principles of the invention.

FIG. 5A illustrates a side view of a first aspect of a third exemplary embodiment of a lighting device comprising multiple light sources in accordance with the principles of the invention.

In this third exemplary embodiment, light device 500 comprises a housing 505 and lens assembly 101 comprising at least one lens 102, 104 forming an optical axis 142 onto which is formed focal point 250.

Further illustrated is lighting assembly 518 positioned at a second end of housing 506. Lighting assembly 518 comprises first lighting module 510/116 (lighting source 510 and controller 116) and second lighting module 512/116 (lighting source 512 and controller 116) positioned along an inner circumference surface of lighting assembly 518 and a light director 515. In this illustrated embodiment, first lighting source 510 and second lighting source 512 are similar to light sources 110, 112 shown and described with regard to FIG. 1B. However, lighting sources 510 and 512 lack one or more of the aperture holder, aperture, dome lens disclosed with regard to first lighting source 110 and second lighting source 112. In this specific illustrated embodiment, lighting sources 510, 512 lack dome lens 136.

In addition, lighting assembly 518 may, as with regard to lighting assembly 418, be removably attachable to housing 505 or integrated into housing 505.

Light director 515 is similar to light director 415, previously described. However, in this illustrated embodiment light director 515 is represented as a clipped pyramid or cone shaped element positioned on base 506. That is, the term "clipped pyramid or clipped cone" represents a geometrical pyramid (or cone) in which a top portion has been removed. When viewed as a 3-dimensional object, light director 515 is in the form of a 3-dimensional trapezoidal shaped object.

Light director 515, which is oriented at a substantially 45-degree angle with respect to optical axis 142, comprises reflective surfaces 440, 442 that operate to redirect light generated by first lighting module 510/116 and second lighting module 512/116, as discussed with regard to FIG. 4B.

Further illustrated is lens 570 positioned substantially perpendicular to optical axis 142. In this illustrated example, lens 570 is positioned in contact with light director 515 and is sized such that light redirected from reflective surfaces 440, 442 is captured by lens 570.

In accordance with this embodiment of the invention, light emitted by first lighting module 510/116 is directed along light path 560 and impinges upon reflective surface 440, which redirects the light along light path 520 toward lens 570. Similarly, light emitted by second lighting module 512/116 is directed along light path 562 and impinges upon reflective surface 442. Reflective surface 442 redirects the light along light path 522 toward lens 570.

Lens 570 concentrates the light directed along light paths 520, 522 toward lens assembly 101, which converges the light onto known point 250, as previously discussed.

Although lens 570 shown in FIG. 5A is depicted as extending a width of lighting assembly 518, it would be understood that lens 570 may be included within a holder that extends the width of lighting assembly 518, wherein the holder retains lens 570 in place and lens 570 may be sized to be sufficient to capture the light redirected by light director 515.

Figure 5B:
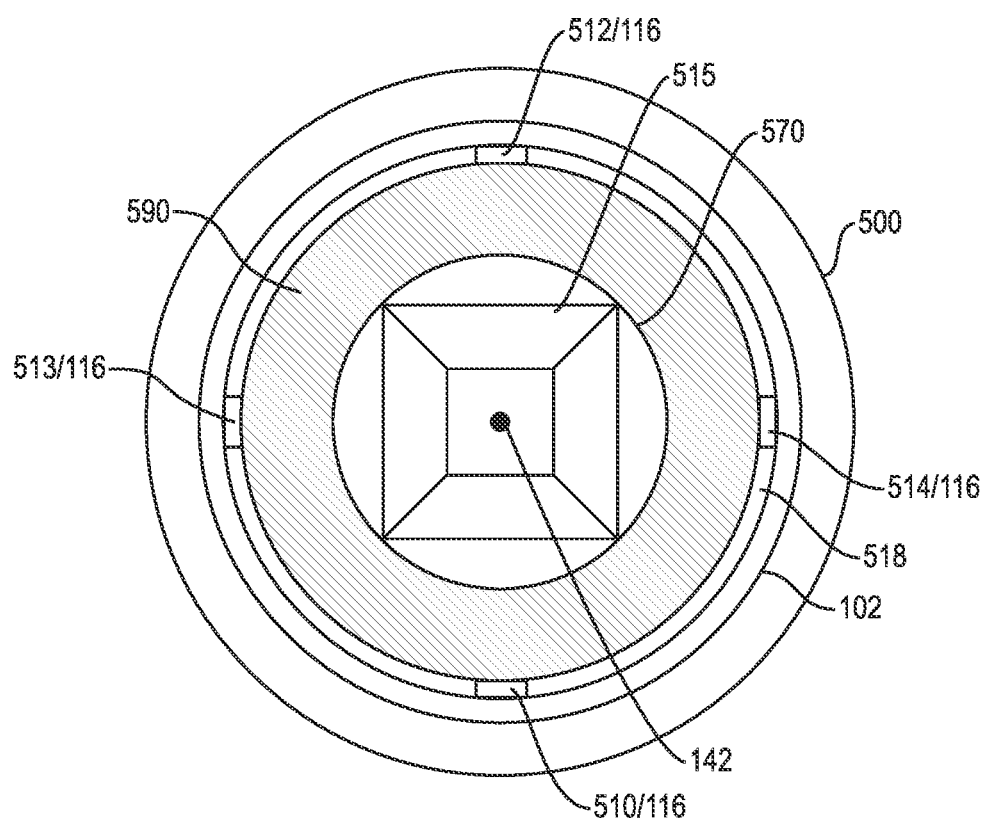
FIG. 5B illustrates a front view of a second aspect of the third exemplary embodiment shown in FIG. 5A.

FIG. 5B illustrates a front view of a second aspect of the third exemplary embodiment shown in FIG. 5A.

In this illustrated front view, a plurality of lighting modules (e.g., first lighting module 510/116, second lighting module 512/116, third lighting module 513/116 and fourth lighting module 514/116) are shown positioned along an inner circumference surface of lighting assembly 518. Further illustrated is light director 515 extending from base 506 of lighting assembly 518, wherein light director 515 is in a shape of a 4-sided clipped pyramid.

Further illustrated is lens 570 positioned substantially perpendicular to the optical axis 142 within holder 590. Holder 590 extends the width of lighting assembly 518 and retains lens 570 in place.

Figure 6:
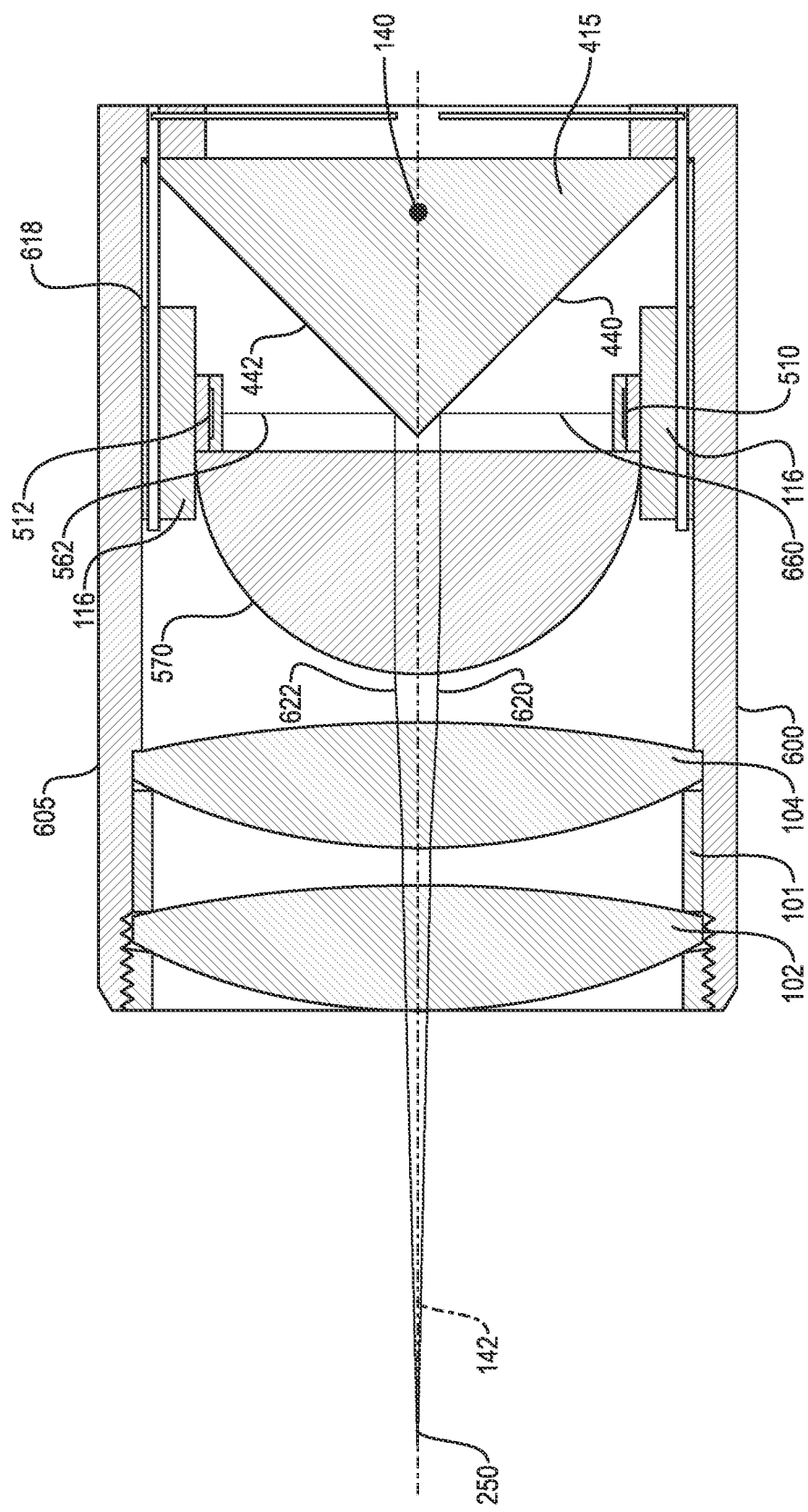
FIG. 6 illustrates a side view of a fourth exemplary embodiment of a lighting device comprising multiple light sources in accordance with the principles of the invention.

FIG. 6 illustrates a side view of a fourth exemplary embodiment of a lighting device comprising multiple light sources in accordance with the principles of the invention.

In this fourth exemplary embodiment, lighting device 600 comprises housing 605 and lens assembly 101 comprising at least one lens 102, 104 forming an optical axis 142.

Further illustrated is lighting assembly 618 comprising first lighting module 510/116 and second lighting module 512/116, positioned along an inner circumference surface of lighting assembly 618 and light director 415.

First lighting module 510/116 and second lighting module 512/116 are similar to those elements described with regard to FIG. 5A and light director 415 is similar to the light director 415 described with regard to FIGS. 4A, 4B.

Light director 415, whose sides or lateral surfaces are oriented at a substantially 45-degree angle with respect to optical axis 142 comprises reflective surfaces 440, 442, which operate to redirect light emitted by first lighting module 510/116 and second lighting module 512/116.

Further illustrated is lens 570 positioned substantially perpendicular to optical axis 142. Lens 570 is sized to capture light redirected from reflective surfaces 440, 442 and direct the capture light toward lens assembly 101.

In this illustrated example, light emitted by first lighting module 510/116 directed along light path 660 and impinges upon reflective surface 440, which redirects light toward lens 570 and lens assembly 101, along light path 620. Similarly, light emitted by second lighting module 512/116 directed along light path 562 impinges upon reflective surface 442, which directs light toward lens 570 and lens assembly 101 along light path 622.

In accordance with the principles of the invention, light directed along light paths 620 and 622 is outputted by lens assembly 101 such that the outputted light converges onto known point 250

Although lens 570 shown in FIG. 6 is depicted as extending the width of optical assembly 618, it would be understood that lens 570 may be included within a holder that extends the width of optical assembly 618 in a manner similar to that shown in FIG. 5B.

Figure 7:
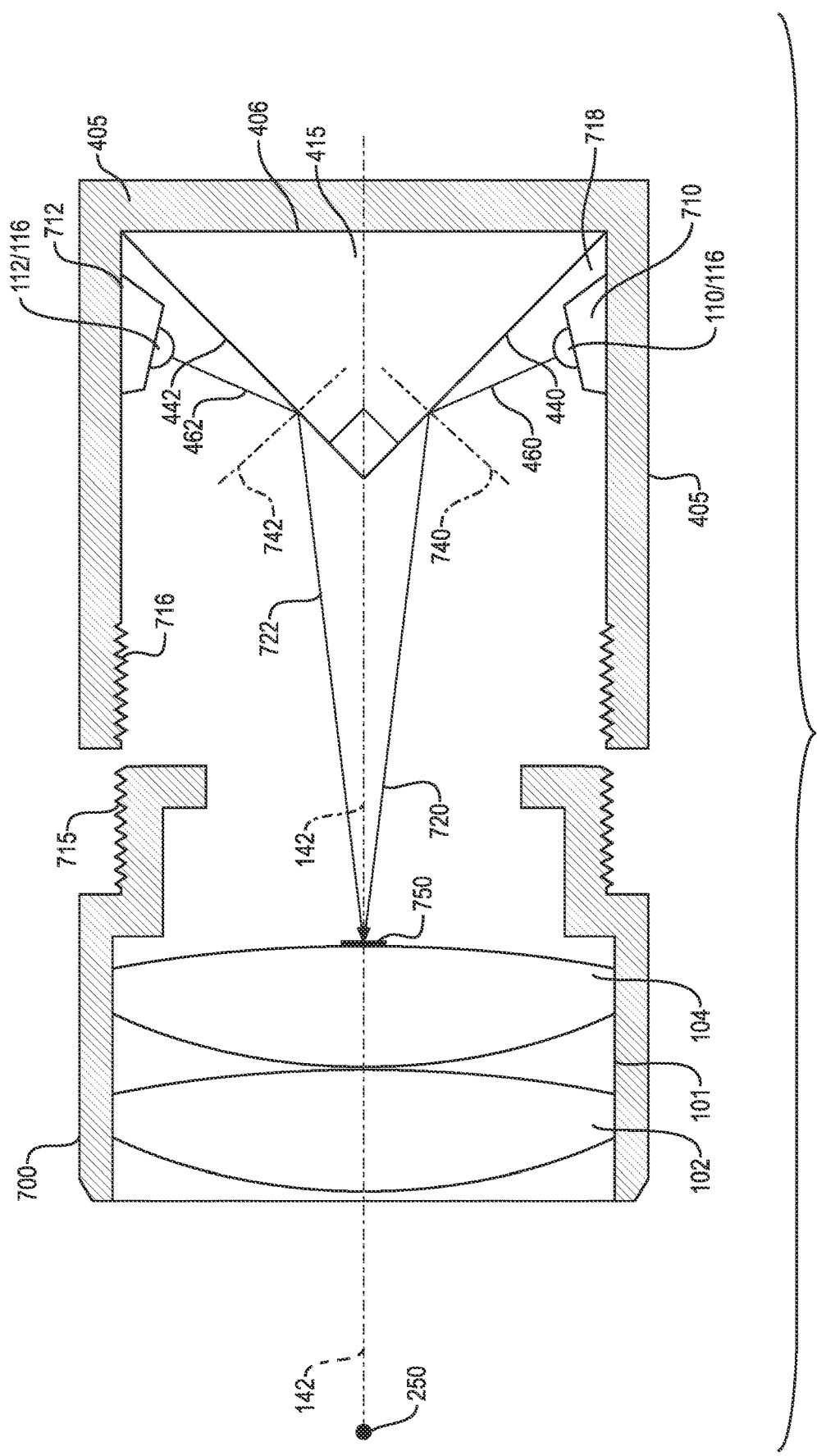
FIG. 7 illustrates a side view of a third aspect of the second exemplary embodiment shown in FIGS. 4A-4C.

FIG. 7 illustrates a side view of a third aspect of the second exemplary embodiment shown in FIGS. 4A-4C, wherein the lighting sources 110, 112 (or lighting modules 110/116, 112/116) are configured to cause light director 415 to redirect light to a known region 750 within lens assembly 101

In this illustrated embodiment, lighting device 700 comprises lighting housing 405 comprising lens housing 101, wherein lens housings 101 includes lens 102 and 104, and lighting assembly 718 includes light director 415, as previously discussed.

In this illustrated embodiment, which is similar to the embodiments shown in FIGS. 4A, 4B, 4C, 5A, 5B, and 6, lens housing 101 may be removably attachable to lighting housing 405, through the illustrated screw thread 715/716. Although a screw thread connection is shown it would be recognized that lens housing 101 and lighting housing 405 may comprise other forms of connections as previously discussed. Similarly, lighting assembly 718 may be removably attachable to housing 405 as shown in FIGS. 1A, 1B, for example.

Further illustrated are reflective surfaces 440 and 442, which reflect light at an angle equal to the angle of the light incident to reflective surfaces 440, 442, with respect to an axis 740, 742 normal to reflective surface 440, 442, respectively.

In this third aspect of the embodiment shown in FIGS. 4A-4C, lighting sources 110 and 112 (or lighting modules 110/116, 112/116) are positioned along the interior surface of lighting housing 405 at an angle 710, 712 with respect to optical axis 142. Accordingly, the light emitted by lighting sources 110, 112 (or lighting modules 110/116, 112/116) is not perpendicular to, but skewed (or slanted from) optical axis 142.

The angle at which light sources 110, 112 (or lighting modules 110/116, 112/116) is offset from the optical axis 142 may be selected or determined to cause the light projected or emitted by lighting sources 110, 112 (or lighting modules 110/116, 112/116) along light paths 460, 462, respectively, to be reflected from reflective surfaces 440, 442 along paths 720, 722 so as to be directed to known region 750 on lens assembly 101.

Region 750 may be determined, in part, based on the characteristics of lens 102, 104 such that the light emitted by lighting sources 110, 112 (or lighting modules 110/116, 112/116) converges at known point 250, as discussed previously.

Figure 8:
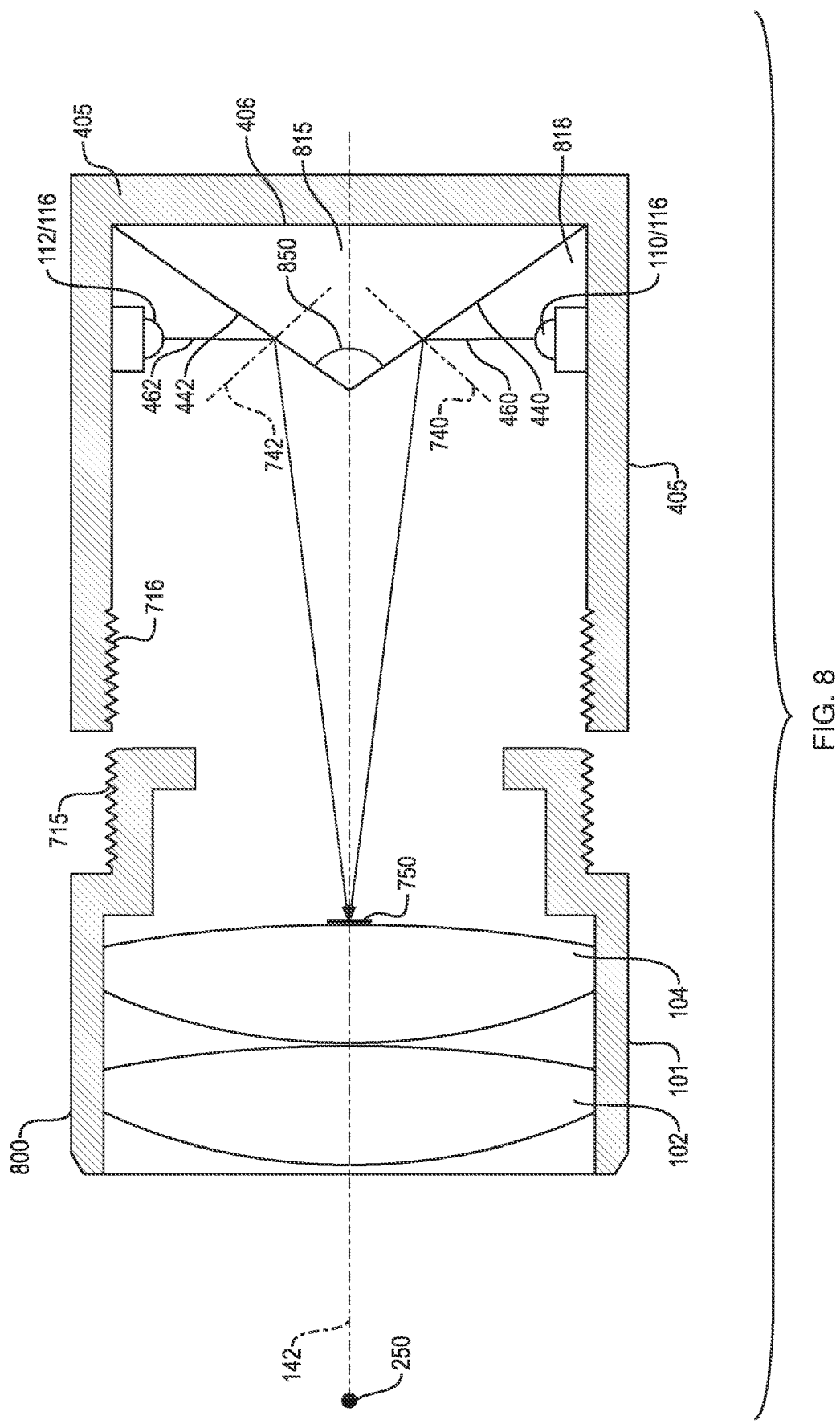
FIG. 8 illustrates a side view of a fourth aspect of the second exemplary embodiment shown in in FIGS. 4A-4C.

FIG. 8 illustrates a side view of a fourth aspect of the second exemplary embodiment shown in in FIGS. 4A-4C.

In this illustrated aspect of the second embodiment shown in FIGS. 4A-4C, lighting device 800 comprises lighting housing 405 comprising lens housing 101, wherein lens housings 101 includes lens 102 and 104, removably attachable to lighting housing 405, and lighting assembly 818, similar to the configuration shown in shown in FIGS. 4A, 4B, comprising lighting sources 110, 112 (lighting modules 110/116, 112/116) positioned about an inner circumference of light assembly 818.

Although, lighting assembly 818 is shown integrated into lighting housing 405, it would be understood that lighting assembly 818 may similarly be removably attachable to lighting housing 405 as shown in FIGS. 1A, 1B, for example.

In accordance with the principles of operation of this illustrated embodiment, light sources 110 and 112 (lighting modules 110/116, 112/116) are arranged along the interior surface of lighting housing 405 (or lighting assembly 818) such that light paths 460, 462 are substantially perpendicular to optical axis 142.

Further illustrated is light director 815, which is similar to light director 415, including reflective surfaces 440, 442, which reflects light projected onto reflective surfaces 440, 442, at an angle equal to the angle of the light incident to light director 815.

In this illustrated embodiment, the peak angle 850 of light director 815, as shown, is an obtuse angle (i.e., greater than 90 degrees) to enable the light emitted by lighting modules 110/116, 112/116, to be reflected toward region 750.

As is known in the art, the light reflected by a reflective surface is reflected at an angle, with respect to a normal (i.e., axis 740, 742) that is equal to the angle of incidence of light.

Figure 9A:
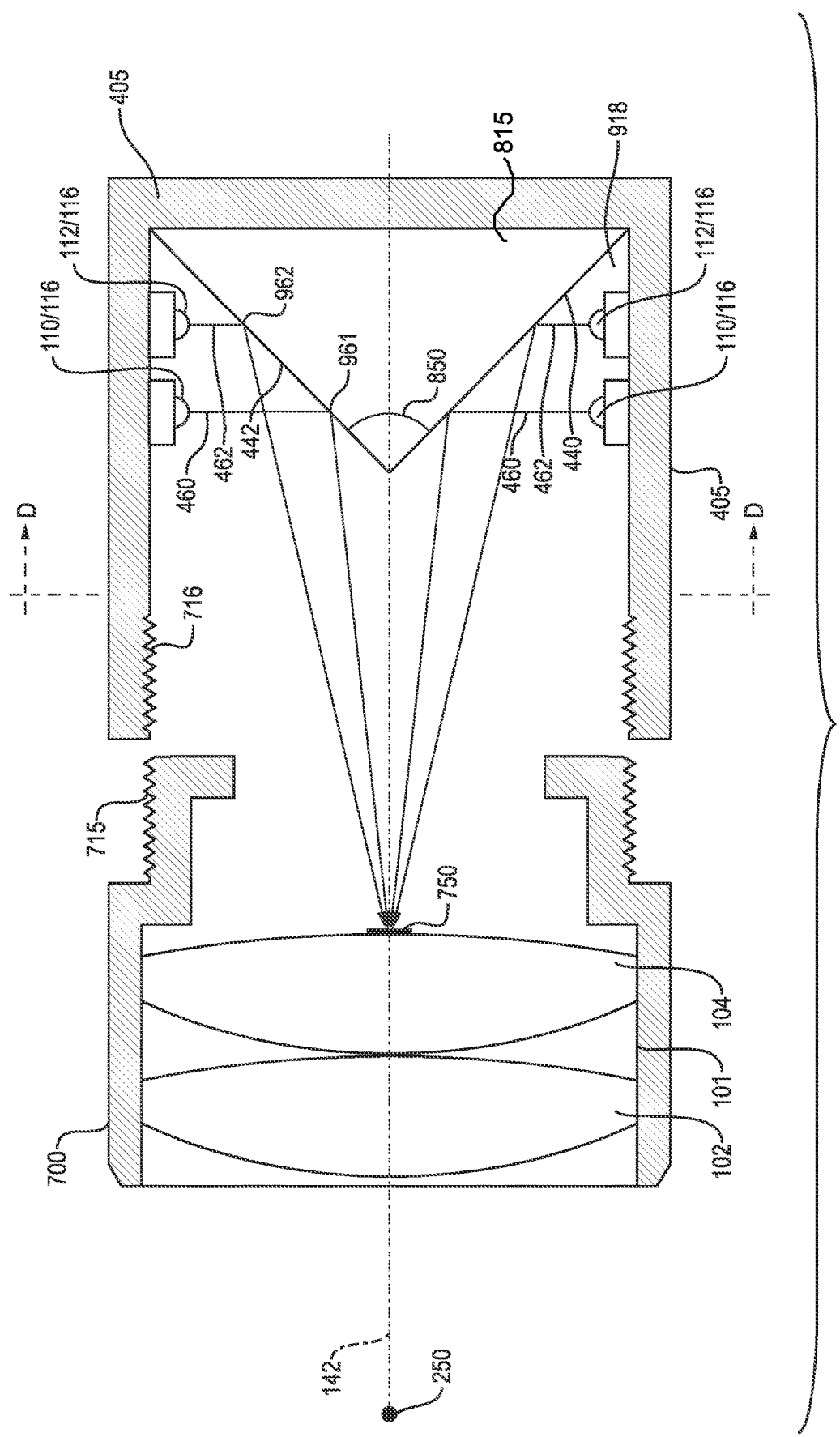
FIG. 9A illustrates a side view of a first aspect of a fifth exemplary embodiment of a lighting device in accordance with the principles of the invention.

FIG. 9A illustrates a side view of a first aspect of a fifth exemplary embodiment of a lighting device in accordance with the principles of the invention.

In this exemplary embodiment, lighting device 900, which is similar to lighting device 400, shown in FIGS. 4A, 4B, comprises a lighting housing 405 comprising a lens assembly 101 comprising at least one objective lens 102, 104 and lighting assembly 918 comprising a plurality of lighting sources 110, 112 (or lighting modules 110/116, 112/116) oriented about an inner circumference of lighting housing 405 and light director 815 comprising a peak angle 850 greater than ninety (90) degrees, as discussed with regard to FIG. 8, to redirect light contacting corresponding points on reflective surfaces 440, 442 towards point 750 on lens assembly 101. Furthermore, lens assembly 101 and lighting assembly 918 may be removably attachable to lighting housing 405, as previously discussed.

In accordance with the principles of this illustrated exemplary embodiment, lighting sources 110 and 112 (lighting modules 110/116, 112/116) are positioned at different points along the inner circumference of lighting assembly 918, such that light emitted by lighting source 110 (lighting module 110/116), projected along light path 460, contacts light director 815 at a first point 961 and light emitted by lighting source 112 projected along light path 462 contacts light director 815 at a second point 962.

The light emitted by lighting source 110 (module 110/116) and lighting source 112 module 112/116) is re-directed toward region 750, as previously discussed.

In one aspect of the invention a plurality of lighting sources 110 (or lighting modules 110/116) may be positioned about an inner circumference of lighting housing 405 in a first plane (in this illustrated case, the plane containing light path 460) and a plurality of second lighting sources 112 (or modules 112/116) may be positioned about an inner circumference of lighting housing 405 in a second plane (in this illustrated case, the plane containing light path 462) wherein the first point of contact 961 of light emitted by lighting source 110 on reflective surfaces 440 is within the first plane, and the second point of contact 962 of light emitted by lighting modules 112/116 on reflective surfaces 442 is within the second plane.

In one aspect of the invention, lighting sources 110 (modules 110/116) may be configured to emit a white light (i.e., violet through red wavelength ranges) while lighting sources 112 (modules 112/116) may be configured to emit light in one or more specific wavelength bands (e.g., ultraviolet, blue, green, yellow, orange, red, etc.).

In another aspect of the invention, lighting sources 110 (module 110/116) may comprise white light emitting elements, and selected ones of lighting sources 112 (module 112/116) may comprise lighting elements emitting light in a wavelength range (e.g., an ultra-violet wavelength range) while selected other ones of lighting sources 112 (module 112/116) may comprise lighting elements emitting light in a different wavelength range, e.g., blue wavelength range.

Figure 9B:
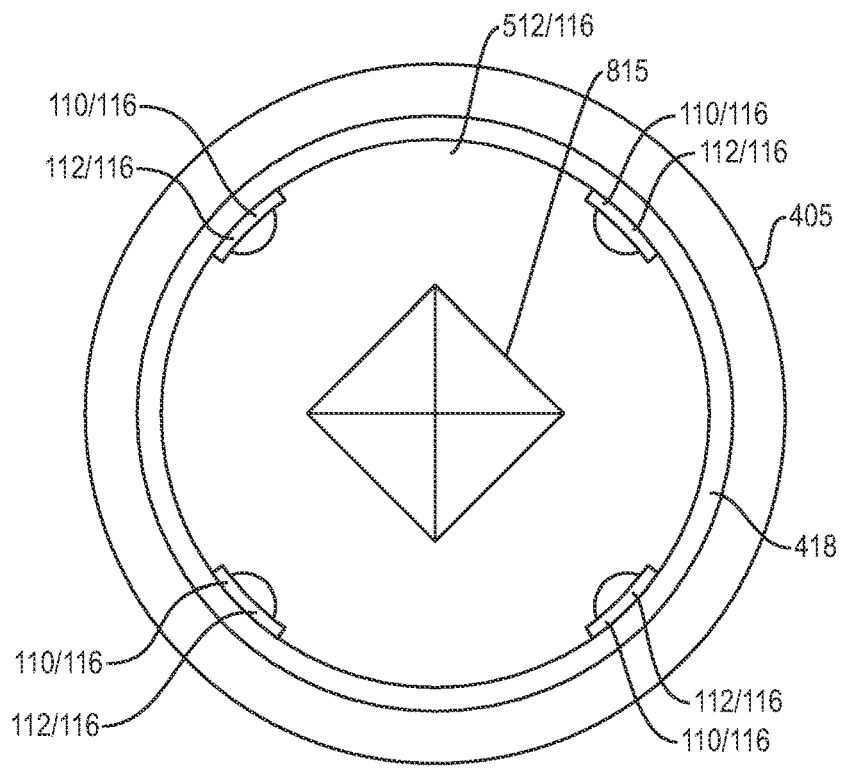
FIG. 9B illustrates a front view of the first aspect of the fifth exemplary embodiment of the lighting device shown in FIG. 9A.

FIG. 9B illustrates a front view of the first aspect of the fifth exemplary embodiment of the lighting device shown in FIG. 9A.

In this illustrated aspect, a plurality of lighting sources 110 (lighting modules 110/116) are arranged about an inner circumference surface of lighting assembly 418 in a first plane. Similarly, a plurality of lighting sources 112 (or lighting modules 112/116) are arranged about an inner circumference of lighting assembly 418, as discussed with regard to FIG. 9A.

In this illustrated example, lighting modules 112/116 are not visible as these modules are positioned behind lighting modules 110/116 as the light emitted by lighting sources 110, 112 are directed toward a same surface of light director 815.

As discussed, light emitted by lighting sources 110, 112 (concurrently, individually or sequentially) is directed toward light director 815, which redirects the light toward lens assembly 101 (not shown), as previously discussed.

Although only four lighting sources 110 (lighting module 110/116) are shown, it would be recognized that the number of lighting modules included along the inner surface of lighting assembly 418 may be increased or decreased based on the number of reflective surfaces of light director 815.

Figure 9C:
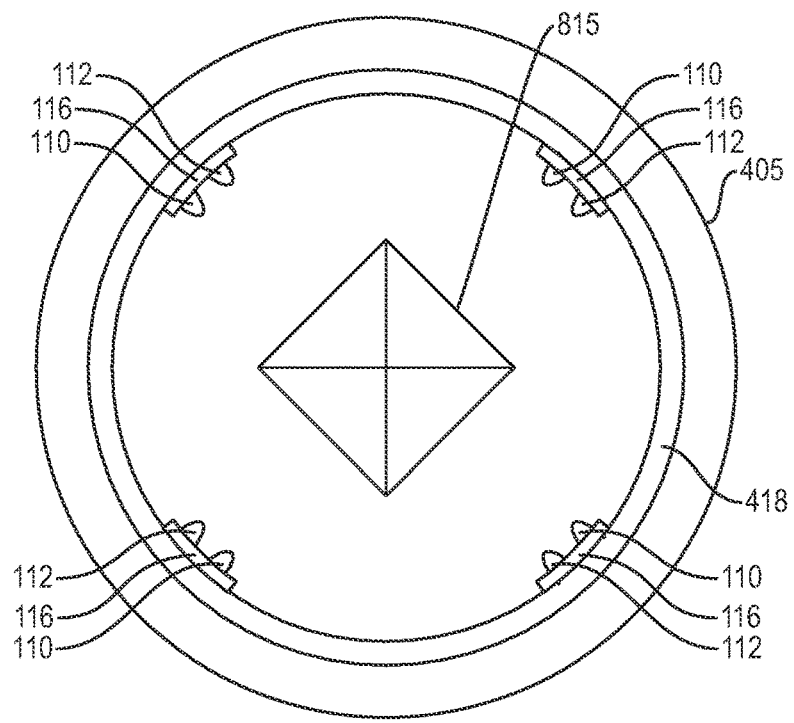
FIG. 9C illustrates a front view of a second aspect of the fifth exemplary embodiment of the lighting device shown in FIG. 9A.

FIG. 9C illustrates a front view, of a second aspect of the fifth exemplary embodiment of the lighting device shown in FIG. 9A.

In this exemplary aspect, a plurality of lighting sources 110 and 112 (lighting modules 110/116, 112/116) are arranged as pairs about an inner circumference surface of lighting assembly 418, wherein the lighting source pair 110/112 are controlled by a same controller 116.

In this exemplary aspect, light emitted by lighting sources 110, 112 (concurrently, individually or sequentially) is directed toward light director 815, which redirects the light toward lens assembly 101 (not shown), as previously discussed.

Although only four lighting modules 110/116 are shown, it would be recognized that the number of lighting modules included along the inner surface of lighting assembly 418 may be increased or decreased based on the number of reflective surfaces of light director 815.

Figure 10:
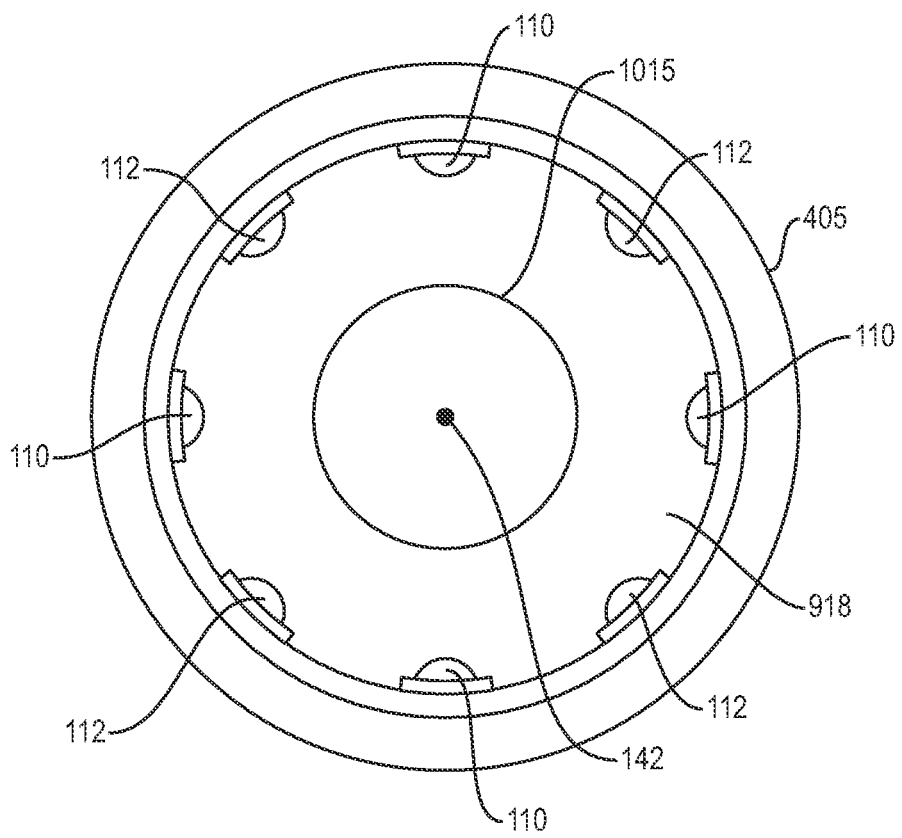
FIG. 10 illustrates a front view of a third aspect of the fifth exemplary embodiment shown in FIG. 9A.

FIG. 10 illustrates a front view of a third aspect of the fifth exemplary embodiment shown in FIG. 9A.

In this illustrated aspect of lighting device 900, lighting device 900 comprises lighting housing 405 including lens housing 101 comprising lens 102 and lighting assembly 918 comprising light director 1015, wherein light director 1015 is shown as a cone or conical element to re-direct light emitted by lighting sources 110, 112 arranged along or about an inner circumference of lighting housing 405. Conical element 1015 is advantageous as it represents a pyramid of an infinite number of sides.

Lighting sources 110, shown along (or about) an inner circumference of lighting housing 405 are arranged in a first plane and lighting sources 112 shown along (or about) an inner circumference of lighting housing 405 are arranged in a second plane (similar to the configuration shown in FIG. 9B). Further illustrated are lighting source 112 offset from lighting modules 110/116.

In still a further aspect of the embodiment shown in FIG. 10, both lighting sources 110 and 112 may be arranged on a same plane (i.e., the first plane and the second plane of FIG. 9B or a single plane of FIG. 4B) wherein the plurality of lighting modules 112/116 may be offset from the lighting modules 110/116.

In this further aspect of the embodiment shown in FIG. 9A, the use of conical shaped light direction 1015 allows for an increase in the number of lighting sources 110, 112 that may be utilized to project light onto focal point 250.

Figure 11:
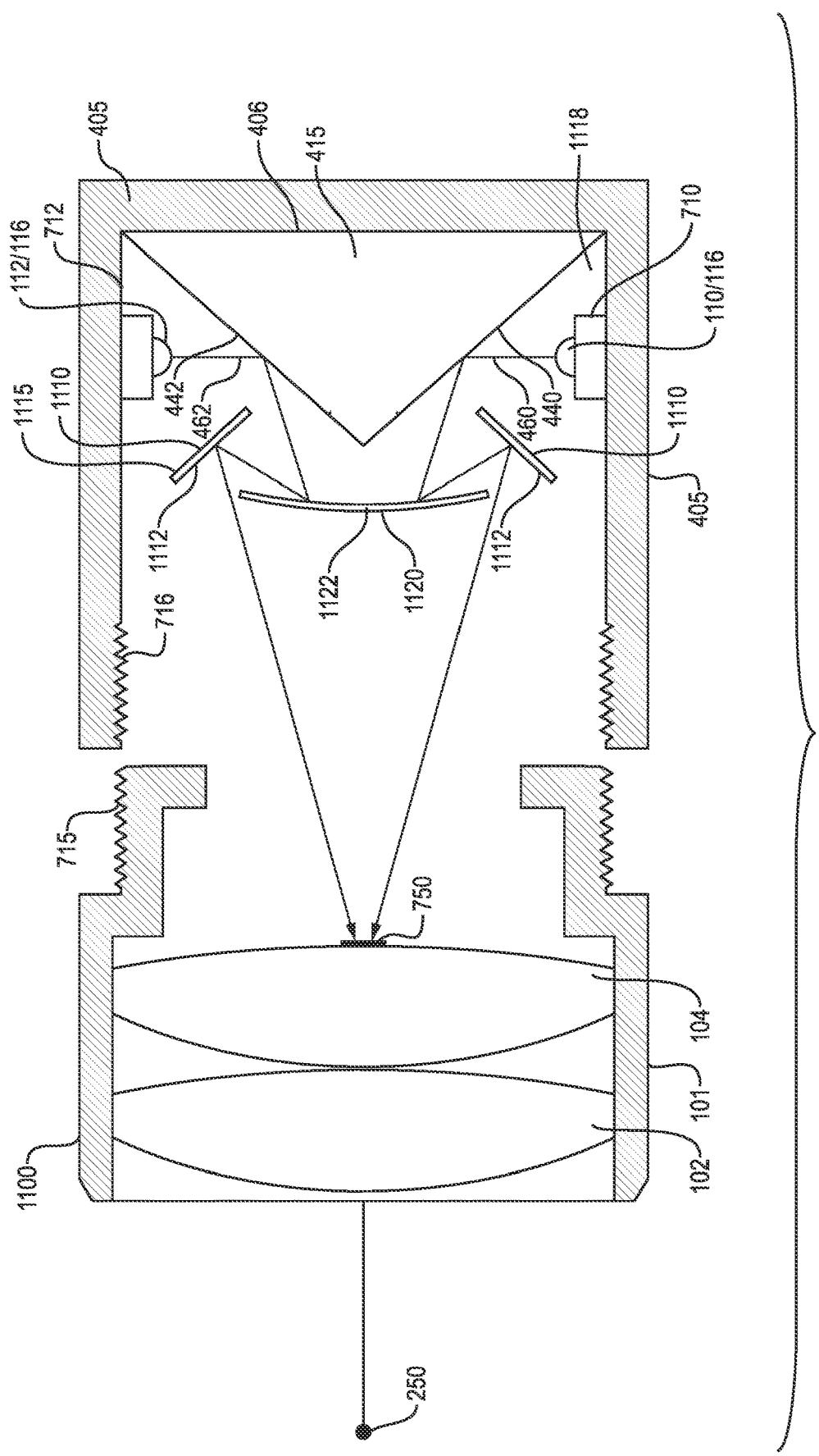
FIG. 11 illustrates a side view of a sixth exemplary embodiment of a lighting device in accordance with the principles of the invention.

FIG. 11 illustrates a side view of a sixth exemplary embodiment of a lighting device in accordance with the principles of the invention.

In this illustrated embodiment, lighting device 1110 comprises lighting housing 405, comprising lens housing 101 and a lighting assembly 1118, similar to that shown in FIGS. 4A, 4B, wherein lens housings 101 includes lens 102 and 104 and lighting housing 1118 includes light director 415 and lighting sources 110 and 112 oriented at an angle 710, 712 with regard to an inner surface of lighting assembly 1118, as discussed with regard to FIG. 7.

Furthermore, as discussed previously, one of lens housing 101 and lighting assembly 1118 may be removably attachable to housing 405 through one of a screw thread (715/716) a snap-fit connection, and a bayonet connection, etc.

In accordance with the principles of operation of this illustrated embodiment, lighting assembly 1118 further includes a reverse conical or parabolic element 1110 including a passthrough 1115 and conical or parabolic section 1120 positioned at or near an apex of light director 415. Reverse conical section 1110 includes reflective surface 1112 and conical section 1120 includes reflective surface 1122

As discussed, the light emitted by lighting modules 110/116, and 112/116, in this case, is re-directed toward conic section 1120. Conic section 1120 then reflects the received light back toward reverse conical section 1110, which directs light towards lens assembly 101.

Lens assembly 101 receiving the light reflected off reflective surfaces 1112 converges the light toward known point 250, as previously discussed.

Although FIG. 11 represents a configuration similar to that disclosed with regard to FIG. 8, wherein the lighting modules 110/116, 112/116 are shown substantially perpendicular to optical axis 142 from lighting assembly 1118, it would be recognized that the principles of FIG. 11 may be applied to the configuration shown in FIG. 7, wherein lighting modules 110/116, 112/116 are offset to optical axis 142, without altering the scope of the invention claimed.

Figure 12:
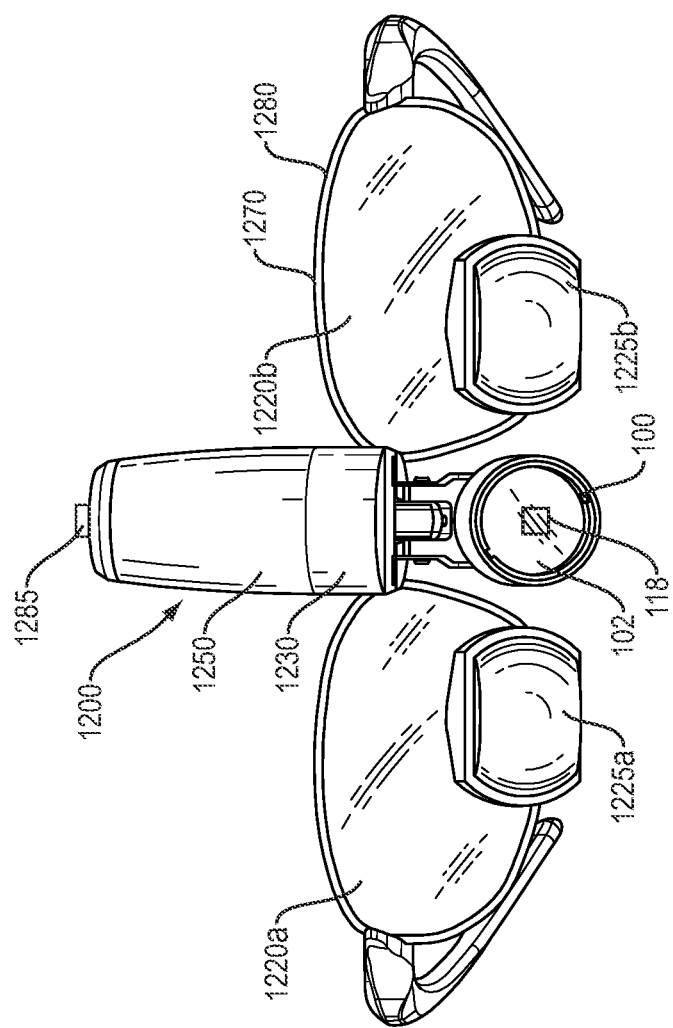
FIG. 12 Illustrates a front view of a head-mounted lighting configuration incorporating the lighting device disclosed herein.

FIG. 12 Illustrates a front view of a head-mounted lighting configuration 1200 comprising an eyewear 1280 comprising a frame 1270 containing a left lens 1220a and a right lens 1220b into which are magnification devices 1225a, 1225b, respectively. Although the head mounted lighting device illustrated refers to an eyewear 1280, it would be understood other types of head mounted light devices are considered within the scope of the invention. For example, U.S. Pat. RE 46463, whose contents have been incorporated by reference, herein, illustrate head mountings, such as a head strap and headband, which are considered within the scope of the term "head mounted".

Lighting configuration 1200 further comprises a battery assembly 1250, an electronics section 1230 and a lighting device 100 as disclosed herein.

Within lighting device 100 is shown, through lens 102, lighting assembly 118 similar to that discussed with regard to FIGS. 1A and 1B.

However, it would be understood by those skilled in the art that while the lighting device 100 shown in FIG. 12 is described with regard to the embodiment of the invention shown in FIGS. 1A, 1B, the lighting devices 400, 500, 600, 700, 800, 900 and 1100 disclosed, herein, may be identified as lighting device 100 in relation to the configuration shown in FIG. 12. Hence, the illustrated lighting assembly 118 may similarly be referred to as lighting assemblies 418, 518, 618, etc.

In accordance with the principles of the invention. the light output from lighting device 100 may be selected to provide one or more different light outputs based on the composition of the lighting sources incorporated into lighting modules 110/116, 112/116, etc.

Further illustrated is a sensing unit 1285 positioned along a top of battery assembly 1250. Sensing unit 1285 may be one of a contact sensor, such as a capacitive touch sensor or a contactless sensor, such as an infra-red (IR) sensor, an ultra-sonic sensor, a proximity sensor, and other similar devices. Although not shown it would be appreciated that sensing unit 1285 may be positioned on or in electrical contact with electronics section 1230.

Battery assembly 1250 incorporates a battery, therein, (not shown) that provides power (electrical energy in the form of a voltage and/or current) to lighting device 100. Although the battery is disclosed with regard to battery assembly 1250, it would be understood that a battery or other source (e.g., AC/DC power converters) providing electrical energy to the lighting sources 110, 112 (or 512, 514), etc., for example, may be remote from the head mounted lighting device 1200. See, for example, U.S. Pat. RE46463, whose contents have been incorporated by reference, herein.

Electronic section 1230 includes circuitry (not shown) that controls the application of the electrical energy (i.e., voltage/current) from the battery (not shown) contained within the illustrated battery assembly 1250 to lighting assembly 118 in lighting device 100. Information from sensing unit 1285 to the circuitry within electronic section 1230 may also provide information suitable for controlling the state of the lighting modules 110/116, 112/116, etc., within lighting element 100.

In accordance with the principles of the invention, light outputted by one or more of the lighting modules 110/116, 112/116 (510/116, 512/116) may be controlled by operation of the sensing element 1285, for example. In one aspect of the invention, wherein each of the lighting modules 110/116, 112/116 (510, 512) generates a white light, sensing element 1285 may operate to turn ON or turn OFF the light generated by each of the modules 110/116, 112/116 (510, 512), individually, sequentially or concurrently. Similarly, in an exemplary configuration wherein first lighting module 110/116, generates light in an ultra-violet (UV) wavelength range and second lighting module 112/116 generates light in a visible (e.g., a blue, a green, a yellow, an orange, a red or a white) wavelength range, sensing element 1285 may operate to turn ON or turn OFF selected ones of the first lighting module 110/116 and second lighting module 112/116 so as to generate different light outputs.

Although the lighting devices 100, 400, 500, 600, 700, 800, 900, and 1100 have been described with regard to two lighting modules, it would be understood that the multi-source lighting configurations shown, herein, may include a plurality of lighting sources suitable for emitting light of different light wavelength ranges (e.g. UV, violet, blue, green, yellow, orange, red, IR, etc.).

In summary, a lighting device is disclosed, which comprises a plurality of lighting modules or sources arranged at an offset angle from an optical axis of a lens assembly, wherein the light is directed toward a lens assembly in a manner that allows for the convergence of the light from the plurality of lighting sources upon a known point. In a second embodiment, a lighting device is disclosed comprising a plurality of lighting modules or sources arranged along an inner circumference surface of the device house and the light generated by the lighting sources is directed to a device for redirecting the light toward a lens assembly in a manner that allows for the convergence of the light from the plurality of lighting sources to a desired point. In accordance with one aspect of the principles of the invention, the light director, receiving light from the lighting modules or sources, may be configured to re-direct the light to a known region to enable the re-directed light to converge to a known point after passing through at least one projection (or objective) lens. In accordance with another aspect of the invention, the lighting sources may be oriented with respect to the light director such that the light emitted by the lighting sources are re-directed by the light director such that the re-directed light is focused onto a known point on the objective lens.

Although the invention has been described with regard to a lighting source, in a preferred embodiment the lighting sources are light emitting diodes (i.e., LEDs), it would be understood that other lighting sources may be incorporated into the invention disclosed without undue modification and, thus, considered within the scope of the invention claimed.

In addition, while the term "lighting module" or "lighting source" has been described with regard to "light emitting diode," it would be recognized that the term "a light emitting diode" may comprise a plurality of light emitting diode elements arranged in one of a matrix or circular pattern. Furthermore, the plurality of light emitting diodes may be within a base dimension of the disclosed dome lens and the positioning of the at least one light emitting diode within a focal length of the dome lens is advantageous as it defocuses and blurs the distinction of the light emitted by the individual light emitting diodes within the array or circular pattern.

Furthermore, the light emitted or output by the light emitting diode(s) is referred to being within a frequency or wavelength range, wherein the wavelength range represents a color (e.g., blue light approximately 400 nanometers to 450 nanometers). However, it would be further understood that light, particularly with regard to light emitting diodes, may be further measured in color temperature, as degrees Kelvin. For example, a soft white light may be measured in a range of 2700° K-3000° K whereas a bright white light may be expressed in a range of 5000° K-6000° K.

Hence, one of ordinary skill in the art would appreciate that the reference to light or emitted light may be measured as frequency, wavelength, color or color temperature, and such terminology of light is incorporated and used interchangeably, herein.

One of ordinary skill in the art will further recognize and appreciate that various modifications and changes can be made without departing from the scope of the invention as set forth in the claims. Accordingly, the specification is to be regarded in an illustrative manner, rather than with a restrictive view, and all such modifications are intended to be included within the scope of the invention. Benefits, other advantages, and solutions to problems have been described above with regard to specific embodiments. The benefits, advantages, and solutions to problems, and any element(s) that may cause any benefits, advantages, or solutions to occur or become more pronounced, are not to be construed as a critical, required, or an essential feature or element of any or all of the claims.

As used herein, the terms "comprises", "comprising", "includes", "including", "has", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "or" refers to an inclusive "or" and not to an exclusive "or". For example, a condition A or B is satisfied by any one of the following: A is true (or present) and B is false (or not present); A is false (or not present) and B is true (or present); and both A and B are true (or present).

The terms "a" or "an" as used herein are to describe elements and components of the invention. This is done for convenience to the reader and to provide a general sense of the invention. The use of these terms in the description herein should be read and understood to include one or at least one. In addition, the singular also includes the plural unless indicated to the contrary. For example, reference to a composition containing "a compound" includes one or more compounds. As used in this specification and the appended claims, the term "or" is generally employed in its sense including "and/or" unless the content clearly dictates otherwise.

All numeric values are herein assumed to be modified by the term "about," whether or not explicitly indicated. The term "about" generally refers to a range of numbers that one of skill in the art would consider equivalent to the recited value (i.e., having the same function or result). In any instances, the terms "about" may include numbers that are rounded (or lowered) to the nearest significant figure. Furthermore, the values presented herein are merely to illustrate the concepts and are not to be considered as the only values that have been contemplated and considered.

It is expressly intended that all combinations of those elements that perform substantially the same function in substantially the same way to achieve the same results are within the scope of the invention. Substitutions of elements from one described embodiment to another are also fully intended and contemplated.

What is claimed is:

1. A head-mounted device for providing directing light toward an object, said device comprising:
   a light assembly comprising:
      at least one housing, each of said at least one housings comprising:
         at least one objective lens arranged on a first side is said housing, said at least one objective lens forming an optical axis substantially perpendicular to said at least one objective lens; and
         a plurality of lighting elements arranged about an inner circumference of said housing, said plurality of lighting elements configured to emit said light;
      a light director extending from a base element of each of said at least one housing, said light director comprising a plurality of reflective surface joined at an apex having an angle greater than 90 degrees, wherein said angle of said apex is determined to direct said light emitted by said plurality of lighting elements toward a known region on said at least one objective lens along said optical axis; and
      an electronic circuit configured to:
         apply a voltage to said plurality of lighting elements; and
   a head-borne device configured to attach to a user's head, wherein said light assembly is configured to:
      attach to said head-borne device.

2. The device of claim 1, wherein selected ones of said plurality of lighting elements comprise:
   at least one light emitting diode;
   a dome lens, wherein said light emitting diode is positioned within a focal length of said dome lens.

3. The device of claim 2, further comprising:
   at least one of: an aperture holder comprising an aperture holder passthrough, and an aperture positioned within the aperture holder, said aperture comprising an aperture passthrough.

4. The device of claim 3, wherein said aperture passthrough is sized to prevent said light emitting diode to passthrough.

5. The device of claim 1, wherein said plurality of lighting elements in at least one of said at least one housing comprises:
   a first set of lighting elements; and
   a second set of lighting element, wherein said first set lighting elements emit said light in a first wavelength band and said second set of lighting elements emit said light within a second wavelength band.

6. The device of claim 5, wherein said first wavelength band and said second wavelength band are one of: overlapping bands and disjoint bands.

7. The device of claim 5, wherein said first set of lighting elements and said second set of lighting elements are within a same plane substantially perpendicular to said optical axis.

8. The device of claim 5, wherein said first set of lighting elements is in a first plane substantially perpendicular to said optical axis and said second set of lighting element is in a second plane substantially perpendicular to said optical axis.

9. The device of claim 1, wherein said plurality of lighting elements emit said light in at least one of: an ultra-violet wavelength range, a visible wavelength range and an infrared wavelength range, wherein said visible wavelength range comprises at least one of: a blue light wavelength range, a green light wavelength range, a yellow light wavelength range, an orange wavelength range, a red-light wavelength range and a white wavelength range.

10. The device of claim 1, wherein said angle of said apex of said light director is based on an orientation of said plurality of lighting elements with respect to said optical axis.

* * * * *